(12) United States Patent
Tsonev et al.

(10) Patent No.: US 7,790,025 B2
(45) Date of Patent: Sep. 7, 2010

(54) EXTERNAL GRADIENT CHROMATOFOCUSING

(75) Inventors: Latchezar I. Tsonev, Gaithersburg, MD (US); Allen G. Hirsh, Silver Spring, MD (US)

(73) Assignee: Cryobiophysica, Inc., Silver Spring, MD (US)

( * ) Notice: Subject to any disclaimer, the term of this patent is extended or adjusted under 35 U.S.C. 154(b) by 858 days.

(21) Appl. No.: 10/556,562

(22) PCT Filed: May 14, 2004

(86) PCT No.: PCT/US2004/015216

§ 371 (c)(1),
(2), (4) Date: Oct. 10, 2006

(87) PCT Pub. No.: WO2004/103519

PCT Pub. Date: Dec. 2, 2004

(65) Prior Publication Data

US 2007/0144973 A1    Jun. 28, 2007

Related U.S. Application Data

(60) Provisional application No. 60/470,889, filed on May 16, 2003, provisional application No. 60/498,287, filed on Aug. 28, 2003.

(51) Int. Cl.
*B01D 15/08* (2006.01)
(52) U.S. Cl. ............... 210/198.2; 210/500.1; 210/501; 210/656
(58) Field of Classification Search ............. 210/635, 210/656, 659, 101, 198.2, 500.1, 501
See application file for complete search history.

(56) References Cited

U.S. PATENT DOCUMENTS 7,425,263 B2 *    9/2008    Tsonev et al. ............ 210/198.2
2004/0023405 A1 *    2/2004    Bevan et al. ................ 436/163

FOREIGN PATENT DOCUMENTS

| EP | 0 172 217 A | 2/1986 |
| EP | 1 273 592 A2 | 1/2003 |
| WO | WO 99/13328 A1 | 3/1999 |

OTHER PUBLICATIONS

Liu (Journal of Chromatography A, 762 (1997) 207-217).*
Fourgeaud, D., "European Search Report" pp. 1-3, from EP 04752276.8, European Patent Office, Rijswijk, The Netherlands (mailed Feb. 13, 2008).
Bates, R.C., et al, "High-performance chromatofocusing using linear and concave pH gradients formed with simple buffer mixtures-I. Effect of buffer composition on the gradient shape" *J. Chromatogr. A*, vol. 890, pp. 25-36 (2000).

(Continued)

*Primary Examiner*—Ernest G Therkorn

(57) ABSTRACT

The invention provides novel methods for the separation of charged molecules such as proteins according to the isoelectric points (pI's) and includes the systems and buffering compositions employed for isolating charged molecules. The invention further provides for modifications to the above described chromatographic methods that enable the separation of charged molecules exhibiting virtually identical pI's by shifting both the buffer's pKa and the pI's of the eluted charged molecules while they are traversing the ion exchange column.

3 Claims, 7 Drawing Sheets

OTHER PUBLICATIONS

Fourgeaud, D., "International Search Report," pp. 1-8, from PCT/US2004/015216, European Patent Office, Rijswijk, The Netherlands (mailed Dec. 2, 2004).

Anderson et al., "Gradient chromatofocusing—mass spectrometry (GCF-MS): Direct MS analysis of proteins using on-line pH gradient ion-exchange chromatography," *Clin. Chem.* 49(6) Suppl.:A11, abs. No. A-31 (2003).

Kang et al., "High-performance cation-exchange chromatofocusing of proteins," *J. Chrom. A* 991:117-128 (2003).

Liu et al., "Gradient chromatofocusing high-performance liquid chromatography I. Practical aspects," *J. Chrom. A* 762:207-217 (1997).

Logan et al., "A Simple, Two-Component Buffer Enhances Use of Chomatofocusing for Processing of Therapeutic Proteins," *Biotechnol. Bioeng.* 62(2):208-215 (1999).

Mhatre et al., "Purification of antibody Fab fragments by cation-exchange chromatography and pH gradient elution," *J. Chrom. A* 707:225-231 (1995).

Shan et al., "Effect of buffer concentration on gradient chromatofocusing performance separating proteins on a high-performance DEAE column," *J. Chrom. A* 909:191-205 (2001).

Shan, "Gradient Chromatofocusing: A New Chromatographic Technique for Protein Purification and Separation," Ph.D. Thesis, Cleveland State University, pp. i-169 (2001).

Walther-Rasmussen et al., "Hydrophobic character of surface regions and total hydrophobicity of four variants of chromosomal class C β-lactamase from *Pseudomonas aeruginosa* are identical. Chromatographic comparison of the hydrophobic character of the variants and the effect of focusing buffer composition on the separation of the variants by chromatofocusing with internal and external pH gradients," *J. Chrom. B* 746:161-172 (2000).

Shan et al., "Gradient Chromatofocusing. Versatile pH Gradient Separation of Proteins in Ion-Exchange HPLC: Characterization Studies," *Anal. Chem.* 74:5641-5649 (2002).

* cited by examiner

Buffer A: 4mM Bis-Tris Propane, 4mM Methyl Piperazine, 4mM Piperazine and 4 mM Triethanolamine pH 9.7 for Mono Q HR 5/5 or pH 10.5 for Mono S HR 5/5. Buffer B: 4mM Bis-Tris Propane, 4mM Methyl Piperazine, 4mM Piperazine, 4 mM Triethanolamine and 2 mM Formic acid pH 2.5

EXTERNAL GRADIENT CHROMATOFOCUSING

RELATED APPLICATIONS

The present application is a U.S. National Phase Application of International
Application PCT/US2004/015216 (filed May 14, 2004) which claims the benefit of U.S. Provisional Application No. 60/470,889 (filed May 16, 2003) and U.S. Provisional Application No. 60/498,287 (filed Aug. 28, 2003), all of which are herein incorporated by reference in their entirety.

BACKGROUND OF THE INVENTION

All publications and patent applications referenced herein are incorporated by reference to the same extent as if each individual publication or patent application was specifically and individually indicated to be incorporated by reference.

1. Field of the Invention

The invention relates to external gradient chromatography. More particularly, the invention relates to novel methods for the separation of charged molecules such as proteins according to their isoelectric points (pI's) and includes the systems and buffering compositions employed for separating such charged molecules.

2. Description of the Related Art

Chromatofocusing is a form of anion exchange chromatography that was first described by Sluyterman and co-workers (see e.g., L. A. AE Sluyterman and O. Elgersma, *Journal of Chromatography A*, 150(1), 1978, 17-30; L. A. AE Sluyterman and J. Wijdenes, *Journal of Chromatography A*, 150 (1), 1978, 31-44; L. A. AE. Sluyterman and J. Wijdenes, *Journal of Chromatography A*, 206(3), 1981, 429-440; L. A. AE. Sluyterman and J. Wijdenes, *Journal of Chromatography A*, 206(3), 1981, 441-447; L. A. AE. Sluyterman and C. Kooistra, *Journal of Chromatography A*, 470(2), 1989, 317-326). In chromatofocusing, a retained pH gradient is automatically generated inside a chromatographic column as a Polybuffer species or other buffering species in the elution solution titrates functional groups on the surface of a weak anion exchanger resin.

Numerous variations of the original Sluyterman approach to chromatofocusing have been published. Most of these techniques are based on a strategy of pre-equilibrating a weak ion exchange column with a starting buffer at one extreme of an intended internal pH gradient. A sample of charged molecules, typically proteins, is introduced at the column entrance. At the initial pH, all of the molecules to be separated have a charge opposite that of the ion exchange resin and thus bind immediately to it. In the discussion below, the molecules to be separated are referred to as proteins, but that should be construed as a preferred aspect. The resin is then perfused with a solution consisting of multi-component buffers at a desired final pH. Due to variations in the binding affinity of the buffering species for the weak ion exchange resin, a retained pH gradient is automatically created inside the column. The gradient on a weak anion exchange resin is an ascending (as opposed to descending on a weak cationic exchange resin) gradient in pH along the length of the column, but a monotonically descending (ascending for weak cationic exchange resin) pH gradient in time. The separation process begins when the final pH buffer enters the column and causes immediate release of a protein because its pH is below the isoelectric point (pI) of that bound protein. The protein then travels through the column until it reaches a pH in an evolving retained pH gradient that is higher than the protein's pI whereupon the protein rebinds to the ion exchange resin. The elution of the protein continues when the monotonically descending pH of the eluent front again reaches the protein's pI and the protein ceases to bind to the ion exchange resin. The protein once again travels down the column until it encounters a pH higher than its pI and again rebinds. This process is continuously repeated until the protein emerges from the column at its pI. Any protein molecule lagging behind the main band will be at a pH such that it has a charge of the same sign as the buffering groups bound to the ion exchange resin. This situation causes the protein to move down the column more quickly than the band itself due to the electrostatic repulsive forces between the identically charged protein and the ion exchange resin-bound buffering groups. Likewise, a protein molecule diffusing ahead of the main band will experience an increase in binding affinity for the ion exchange resin and will consequently move slower than the main band. The total result is a powerful focusing effect that, under optimal conditions, allows separations of proteins whose pI's differ by as little as 0.02 pH units.

The effective range of pH of the most widely used chromatofocusing technique utilizes commercially available special Polybuffers (e.g. Pharmalyte 8-10.5, Polybuffer 96 and Polybuffer 74) and weak exchange resins (e.g. Mono P, PBE94 and PBE 118) and is about 3 pH units, typically in the ranges 9 to 6 or 7 to 4. The Polybuffers are expensive and bind strongly enough to proteins to make their removal from the purified protein a significant problem. As a result, this potentially extraordinarily valuable fast purification technique has been limited to a laboratory purification technique that finds little practical application in bulk industrial protein purification.

Several groups have tried to overcome these limitations with relatively simple buffer solutions as eluents but still employing either specially designed or commonly available weak anion exchanger resins. The most successful of these systems (Logan et al, *Biotechnology and Bioengineering*, 62(2), 1999) utilizes a two component elution buffer of common, easily removed buffer components useful down to a pH as low as 5.0 to create an evolving retained gradient in a weak anionic column with an initial pH as high as 9.5. This system works well enough over the pH range described to show that high volume chromatofocusing is feasible. There is, however, no external control of the gradient generated in Logan's method.

The few publications that have urged the use of external gradients and a small number of inexpensive buffers in combination with weak anionic columns report a maximum effective pH gradient range of 3.5 units, which is 20% less then that reported by Logan et al. (see e.g., Yansheng Liu and David J. Anderson, *Journal of Chromatography A*, 762(1-2), 1997, 207-217; Yansheng Liu and David J. Anderson, *Journal of Chromatography A*, 762(1-2), 1997, 47-54; Lian Shan and David J. Anderson, *Journal of Chromatography A*, 909(2), 2001, 191-205; Ronald C. Bates et al., *Journal of Chromatography A*, 890(1), 2000, 25-36; Xuezhen Kang et al., *Journal of Chromatography A*, 890(1), 2000, 37-43; Douglas D. Frey et al., U.S. Pat. No. 5,851,400); Jan Walther-Rasmussen and Niels Høoby, *Journal of Chromatography B*, 746(2), 2000, 161-172).

SUMMARY OF THE INVENTION

An aspect of the invention is to provide novel methods for the chromatographic separation of charged molecules such as proteins according to their isoelectric points. A second object of the invention is to provide a novel chromatography system for use with low or high pressure liquid chromatography that comprises an automated feedback-controlled external pH gradient generating system.

In another aspect of the invention, there is provided a method of chromatographically separating charged molecules having different isoelectric points, comprising:

adding the charged molecules to be separated to an anion exchange adsorbent perfused with a solvent comprising at least three buffering components at an initial pH where the anion exchange adsorbent has a charge opposite that of the charged molecules;

supplying to the anion exchange adsorbent an eluent formed with a time dependent pH formed from the continuous mixing of a solution at the initial pH containing the at least three buffering components pumped out from a first reservoir with a solution at pH different from the initial pH containing the at least three buffering components pumped out from a second reservoir, wherein the mixing proportions vary to maintain an unretained pH gradient with an externally defined slope; and collecting the charged molecules, each of which separately elutes from the anion exchange adsorbent at its effective isoelectric point.

In another aspect of the invention, there is provided a method of chromatographically separating charged molecules having different isoelectric points, comprising:

adding the charged molecules to be separated to a cation exchange adsorbent perfused with a solvent comprising buffering components at an initial pH where the cation exchange adsorbent has a charge opposite that of the charged molecules;

supplying to the cation exchange adsorbent an eluent with a time dependent pH formed from the continuous mixing of a solution at the initial pH containing the buffering components pumped out from a first reservoir with a solution at pH different from the initial pH containing the buffering components pumped out from a second reservoir, wherein the mixing proportions vary to maintain an unretained pH gradient with an externally defined slope; and collecting the charged molecules, each of which separately elutes from the cation exchange adsorbent at its effective isoelectric point.

In another aspect of the invention, there is provided a chromatofocusing method of chromatographically separating charged molecules having different isoelectric points, comprising:

adding the charged molecules to be separated to an anion exchange adsorbent perfused with a solvent comprising at least three buffering components at an initial maximum pH where the anion exchange adsorbent has a charge opposite that of the charged molecules;

supplying to the anion exchange adsorbent an eluent with a time dependent pH formed from the continuous mixing of a solution at the initial pH containing the at least three buffering components with or without additional buffering components pumped out from a first reservoir with a solution at a different pH containing the at least three buffering components with or without additional buffering components pumped out from a second reservoir, wherein the mixing proportions vary to maintain an unretained pH gradient with an externally defined slope; and collecting the charged molecules, each of which separately elutes from the anion exchange adsorbent at its effective isoelectric point.

In another aspect of the invention, there is provided a reverse chromatofocusing method of chromatographically separating charged molecules having different isoelectric points, comprising:

adding the charged molecules to be separated to a cation exchange adsorbent perfused with a solvent comprising buffering components at an initial pH where the cation exchange adsorbent has a charge opposite that of the charged molecules;

supplying to the cation exchange adsorbent an eluent with a time dependent pH formed from the continuous mixing of a solution at the initial pH containing the buffering components with or without additional buffering components pumped out from a first reservoir with a solution at a pH different from the initial pH containing the buffering components with or without additional buffering components pumped out from a second reservoir, wherein the mixing proportions vary to maintain an unretained pH gradient with an externally defined slope; and collecting the charged molecules, each of which separately elutes from the cation exchange adsorbent at its effective isoelectric point.

In yet another aspect of the invention, there is provided a method of chromatographically separating charged molecules having different isoelectric points, comprising: adding the charged molecules to an ion exchange adsorbent at a temperature $T_0$;

perfusing the ion exchange absorbent with a solvent comprising buffering components at an initial pH where the ion exchange adsorbent has a charge opposite that of the charged molecules;

changing the temperature of the ion exchange adsorbent to $T_1$;

supplying to the ion exchange adsorbent an eluent with a time dependent pH formed from the continuous mixing of a solution at the initial pH containing the buffering components pumped out from a first reservoir with a solution at pH different from the initial pH containing the buffering components pumped out from a second reservoir, wherein the mixing proportions vary to maintain an unretained pH gradient with an externally defined slope; and collecting the charged molecules, each of which separately elutes from the ion exchange adsorbent at its effective isoelectric point, wherein the difference between $T_0$ and $T_1$ is between 0° C. and 80° C.

In another aspect of the invention, there is provided a method of chromatographically separating charged molecules having different isoelectric points, comprising:

perfusing an ion exchange adsorbent at a temperature $T_0$ with a solvent comprising buffering components at an initial pH where the ion exchange adsorbent has a charge opposite that of the charged molecules to be separated;

changing the temperature of the ion exchange adsorbent to $T_1$;

adding the charged molecules to be separated to the ion exchange adsorbent;

supplying to the ion exchange adsorbent an eluent with a time dependent pH formed from the continuous mixing of a solution at the initial pH containing the buffering components pumped out from a first reservoir with a solution at pH different from the initial pH containing the buffering components pumped out from a second reservoir, wherein the mixing proportions vary to maintain an unretained pH gradient with an externally defined slope; and collecting the charged molecules, each of which separately elutes from the ion exchange adsorbent at its effective isoelectric point, wherein the difference between $T_0$ and $T_1$ is between 0° C. and 80° C.

In another aspect of the invention, there is provided a combined external gradient chromatofocusing method of chromatographically separating charged molecules having different isoelectric points, comprising:

applying and binding the charged molecules to be separated to an anion exchange adsorbent perfused with a solvent comprising at least one buffering component at an initial maximum pH where the anion exchange adsorbent has a charge opposite that of the charged molecules;

connecting a cation exchange adsorbent in series after the anion exchange adsorbent and equilibrating both exchangers at the initial maximum pH;

supplying to the anion exchange adsorbent an eluent with a time dependent pH formed from the continuous mixing of a solution at the initial pH containing the at least one buffering component pumped out from a first reservoir with a solution at a different pH containing the at least one buffering component pumped out from a second reservoir, wherein the mixing proportions vary to maintain an unretained pH gradient with an externally defined slope;

eluting the charged molecules, each of which separately elutes from the anion exchange adsorbent at its effective isoelectric point until a predetermined minimum pH is reached and;

directing the resulting effluent from the anion exchange adsorbent containing the charged molecules into the cation exchange adsorbent to be further separated and;

binding the charged molecules that are positively charged to the cation exchange adsorbent until the predetermined minimum pH is reached;

removing the anion exchange adsorbent, reversing the pH gradient perfusing the cation exchange adsorbent to develop from a predetermined minimum pH to a predetermined maximum pH; and collecting the charged molecules, each of which separately elutes from the cation exchange adsorbent at its effective isoelectric point, until the predetermined maximum pH is reached.

In another aspect of the invention, there is provided a combined external gradient chromatofocusing method of chromatographically separating charged molecules having different isoelectric points, comprising:

applying and binding the charged molecules to be separated to a cation exchange adsorbent perfused with a solvent comprising at least one buffering component at an initial minimum pH where the cation exchange adsorbent has a charge opposite that of the charged molecules;

connecting an anion exchange adsorbent in series after the cation exchange adsorbent and equilibrating both exchangers at the initial minimum pH;

supplying to the cation exchange adsorbent an eluent with a time dependent pH formed from the continuous mixing of a solution at the initial pH containing the at least one buffering component pumped out from a first reservoir with a solution at a different pH containing the at least one buffering component pumped out from a second reservoir, wherein the mixing proportions vary to maintain an unretained pH gradient with an externally defined slope;

eluting the charged molecules, each of which separately elutes from the cation exchange adsorbent at its effective isoelectric point until a predetermined maximum pH is reached;

directing the resulting effluent from the cation exchange adsorbent containing the charged molecules into the anion exchange adsorbent to be further separated and;

binding the charged molecules that are negatively charged to the anion exchange adsorbent until the predetermined maximum pH is reached;

removing the cation exchange adsorbent;

reversing the pH gradient perfusing the anion exchange adsorbent from a predetermined maximum pH to a predetermined minimum pH; and collecting the charged molecules, each of which separately elutes from the anion exchange adsorbent at its effective isoelectric point until the predetermined minimum pH is reached.

In another aspect of the invention, there is provided a combined external gradient chromatofocusing method of chromatographically separating charged molecules having different isoelectric points, comprising:

applying the charged molecules to be separated to an anion exchange adsorbent, which is followed by a cation exchange adsorbent connected in series such that the two adsorbents are perfused with a solvent comprising at least one buffering component at an initial pH, where each of the charged molecules to be separated fall into one of three charge classes: negatively charged for those charged molecules that have apparent pIs below the initial pH; neutral for those charged molecules that fail to bind to either the anion exchange adsorbent or the cation exchange adsorbent at the initial pH; and positively charged for those charged molecules that have apparent pIs above the initial pH;

binding the charged molecules which are negatively charged at the initial pH to the anion adsorbent;

binding the charged molecules which are positively charged at the initial pH to the cation adsorbent;

collecting those charged molecules which fail to bind to either the cation exchange adsorbent or the anion exchange adsorbent at the initial pH;

disconnecting the anion exchange adsorbent and the cation exchange adsorbent from each other at the initial pH;

supplying to the anion exchange adsorbent an eluent with a time dependent decreasing pH starting at the initial pH formed from the continuous mixing of a solution at the initial pH containing the at least one buffering component pumped out from a first reservoir with a solution at a different pH containing the at least one buffering component pumped out from a second reservoir, wherein the mixing proportions vary to maintain an unretained pH gradient with an externally defined slope;

collecting the charged molecules, each of which separately elutes from the anion exchange adsorbent at its effective isoelectric point, until a final minimum pH is reached;

supplying to the cation exchange adsorbent an eluent with a time dependent increasing pH starting at the initial pH formed from the continuous mixing of a solution at the initial pH containing the at least one buffering component pumped out from a first reservoir with a solution at a different pH containing the at least one buffering component pumped out from a second reservoir, wherein the mixing proportions vary to maintain an unretained pH gradient with an externally defined slope; and collecting the charged molecules, each of which separately elutes from the cation exchange adsorbent at its effective isoelectric point until a final maximum pH is reached.

In another aspect of the invention, there is provided a combined external gradient chromatofocusing method of chromatographically separating charged molecules having different isoelectric points, comprising:

applying the charged molecules to be separated to a cation exchange adsorbent, which is followed by an anion exchange adsorbent connected in a series such that the two adsorbents are perfused with a solvent comprising at least one buffering component at an initial pH where each of the charged molecules to be separated fall into one of the three charge classes: negatively charged for those charged molecules that have apparent pIs below the initial pH; neutral for those charged molecules that fail to bind to either the anion exchange adsorbent or the cation exchange adsorbent at the initial pH; and positively charged for those charged molecules that have apparent pIs above the initial pH;

binding the charged molecules which are positively charged at the initial pH to the cation adsorbent;

binding the charged molecules which are negatively charged at the initial pH to the anion adsorbent;

collecting those charged molecules which fail to bind to either the cation exchange adsorbent or the anion exchange adsorbent at the initial pH;

disconnecting the cation exchange adsorbent and anion exchange adsorbent from each other at the initial pH;

supplying to the cation exchange adsorbent an eluent with a time dependent increasing pH starting at the initial pH formed from the continuous mixing of a solution at the initial pH containing the at least one buffering component pumped out from a first reservoir with a solution at a different pH containing the at least one buffering component pumped out from a second reservoir, wherein the mixing proportions vary to maintain an unretained pH gradient with an externally defined slope;

collecting the charged molecules, each of which separately elutes from the cation exchange adsorbent at its effective isoelectric point until a final maximum pH is reached;

supplying to the anion exchange adsorbent an eluent with a time dependent decreasing pH starting at the initial pH formed from the continuous mixing of a solution at the initial pH containing the at least one buffering component pumped out from a first reservoir with a solution at a different pH containing the at least one buffering component pumped out from a second reservoir, wherein the mixing proportions vary to maintain an unretained pH gradient with an externally defined slope; and collecting the charged molecules, each of which separately elutes from the anion exchange adsorbent at its effective isoelectric point, until a final minimum pH is reached.

In another aspect of the invention, there is provided a combined external gradient chromatofocusing method of chromatographically separating charged molecules having different isoelectric points, comprising:

applying and binding the charged molecules to be separated to an anion exchange adsorbent perfused with a solvent comprising at least one buffering component at an initial maximum pH and at a temperature $T_0$ where the anion exchange adsorbent has a charge opposite that of the charged molecules;

connecting a cation exchange adsorbent in series after the anion exchange adsorbent, changing the temperature of the cation exchange adsorbent to $T_1$ and equilibrating both exchangers at the initial maximum pH as measured in the solvent at the temperature $T_0$;

supplying to the anion exchange adsorbent an eluent at the temperature $T_0$ with a time dependent pH formed from the continuous mixing of a solution at the initial pH containing the at least one buffering component pumped out from a first reservoir with a solution at a different pH containing the at least one buffering component pumped out from a second reservoir, wherein the mixing proportions vary to maintain an unretained pH gradient with an externally defined slope;

eluting the charged molecules, each of which separately elutes from the anion exchange adsorbent at its effective isoelectric point, until a predetermined minimum pH is reached at the temperature $T_0$;

directing the resulting effluent from the anion exchange adsorbent containing the charged molecules into the cation exchange adsorbent to be further separated at the temperature $T_1$;

binding the charged molecules that are positively charged to the cation exchange adsorbent until the predetermined minimum pH is reached at the temperature $T_0$;

removing the anion exchange adsorbent;

reversing the pH gradient perfusing the cation exchange adsorbent to develop from a predetermined minimum pH to a predetermined maximum pH at the temperature $T_1$; and collecting the charged molecules, each of which separately elutes from the cation exchange adsorbent at its effective isoelectric point, until the predetermined maximum pH is reached at the temperature $T_1$.

In another aspect of the invention, there is provided a combined external gradient chromatofocusing method of chromatographically separating charged molecules having different isoelectric points, comprising:

applying and binding the charged molecules to be separated to a cation exchange adsorbent perfused with a solvent comprising at least one buffering component at an initial minimum pH and at a temperature $T_0$ where the cation exchange adsorbent has a charge opposite that of the charged molecules;

connecting an anion exchange adsorbent in series after the cation exchange adsorbent, changing the temperature of the anion exchange adsorbent to $T_1$ and equilibrating both exchangers at the initial minimum pH as measured in the solvent at the temperature $T_0$;

supplying to the cation exchange adsorbent an eluent with a time dependent pH at the temperature $T_0$ formed from the continuous mixing of a solution at the initial pH containing the at least one buffering component pumped out from a first reservoir with a solution at a different pH containing the at least one buffering component pumped out from a second reservoir, wherein the mixing proportions vary to maintain an unretained pH gradient with an externally defined slope;

eluting the charged molecules, each of which separately elutes from the cation exchange adsorbent at its effective isoelectric point, until a predetermined maximum pH is reached at the temperature $T_0$;

directing the resulting effluent from the cation exchange adsorbent containing the charged molecules into the anion exchange adsorbent to be further separated at the temperature $T_1$;

binding the charged molecules that are negatively charged to the anion exchange adsorbent until the predetermined maximum pH is reached at the temperature $T_0$;

removing the cation exchange adsorbent;

reversing the pH gradient perfusing the anion exchange adsorbent to develop from a predetermined maximum pH to a predetermined minimum pH at the temperature $T_1$; and collecting the charged molecules, each of which separately elutes from the anion exchange adsorbent at its effective isoelectric point, until the predetermined minimum pH is reached at the temperature $T_1$.

In another aspect of the invention, there is provided a combined external gradient chromatofocusing method of chromatographically separating charged molecules having different isoelectric points, comprising:

applying and binding the charged molecules to be separated to an anion exchange adsorbent perfused with a solvent comprising at least one buffering component at an initial maximum pH and a temperature $T_0$ where the anion exchange adsorbent has a charge opposite that of the charged molecules;

connecting a cation exchange adsorbent in series after the anion exchange adsorbent, changing the temperature to $T_1$ and equilibrating both exchangers at a changed initial maximum pH at the temperature $T_0$;

supplying to the anion exchange adsorbent an eluent at the temperature $T_1$ with a time dependent pH formed from the continuous mixing of a solution at the initial pH containing the at least one buffering component pumped out from a first reservoir at the temperature $T_1$ with a solution at a different pH containing the at least one buffering component pumped out from a second reservoir at the temperature $T_1$, wherein the mixing proportions vary to maintain an unretained pH gradient with an externally defined slope;

eluting the charged molecules, each of which separately elutes from the anion exchange adsorbent at its effective isoelectric point until a predetermined minimum pH is reached at the temperature $T_1$;

directing the resulting effluent from the anion exchange adsorbent containing the charged molecules into the cation exchange adsorbent to be further separated at the temperature $T_1$;

binding the charged molecules that are positively charged to the cation exchange adsorbent until the predetermined minimum pH is reached at the temperature $T_1$;

removing the anion exchange adsorbent;

reversing the pH gradient perfusing the cation exchange adsorbent to develop from a predetermined minimum pH to a predetermined maximum pH at the temperature $T_1$; and collecting the charged molecules, each of which separately elutes from the cation exchange adsorbent at its effective isoelectric point until the predetermined maximum pH is reached at the temperature $T_1$.

In another aspect of the invention, there is provided a combined external gradient chromatofocusing method of chromatographically separating charged molecules having different isoelectric points, comprising:

applying and binding the charged molecules to be separated to a cation exchange adsorbent perfused with a solvent comprising at least one buffering component at an initial minimum pH and at a temperature $T_0$ where the cation exchange adsorbent has a charge opposite that of the charged molecules;

connecting an anion exchange adsorbent in series after the cation exchange adsorbent, changing the temperature to $T_1$ and equilibrating both exchangers at a changed initial maximum pH at the temperature $T_1$;

supplying to the cation exchange adsorbent an eluent with a time dependent pH at the temperature $T_1$ formed from the continuous mixing of a solution at the initial pH containing the at least one buffering component pumped out from a first reservoir at the temperature $T_1$ with a solution at a different pH containing the at least one buffering component pumped out from a second reservoir at the temperature $T_1$, wherein the mixing proportions vary to maintain an unretained pH gradient with an externally defined slope;

eluting the charged molecules, each of which separately elutes from the cation exchange adsorbent at its effective isoelectric point until a predetermined maximum pH is reached at the temperature $T_1$;

directing the resulting effluent from the cation exchange adsorbent containing the charged molecules into the anion exchange adsorbent to be further separated at the temperature $T_1$;

binding the charged molecules that are negatively charged to the anion exchange adsorbent until the predetermined maximum pH is reached at the temperature $T_1$;

removing the cation exchange adsorbent;

reversing the pH gradient perfusing the anion exchange adsorbent to develop from a predetermined maximum pH to a predetermined minimum pH at the temperature $T_1$; and collecting the charged molecules, each of which separately elutes from the anion exchange adsorbent until the predetermined minimum pH is reached at the temperature $T_1$.

In another aspect of the invention, there is provided a combined external gradient chromatofocusing method of chromatographically separating charged molecules having different isoelectric points, comprising:

applying and binding the charged molecules to be separated to an anion exchange adsorbent perfused with a solvent comprising at least one buffering component at an initial maximum pH and at a temperature $T_0$ where the anion exchange adsorbent has a charge opposite that of the charged molecules;

connecting a cation exchange adsorbent in series after the anion exchange adsorbent, changing the temperature of the cation exchanger to $T_1$ and equilibrating both exchangers at the initial maximum pH as measured at the temperature $T_0$;

supplying to the anion exchange adsorbent an eluent at the temperature $T_0$ with a time dependent pH formed from the continuous mixing of a solution at the initial pH containing the at least one buffering component pumped out from a first reservoir with a solution at a different pH containing the at least one buffering component pumped out from a second reservoir, wherein the mixing proportions vary to maintain an unretained pH gradient with an externally defined slope;

eluting the charged molecules, each of which separately elutes from the anion exchange adsorbent at its effective isoelectric point, until a predetermined minimum pH is reached at the temperature $T_0$;

directing the resulting effluent from the anion exchange adsorbent containing the charged molecules into the cation exchange adsorbent to be further separated at the temperature $T_1$;

binding the charged molecules that are positively charged to the cation exchange adsorbent until the predetermined minimum pH is reached at the temperature $T_0$;

removing the anion exchange adsorbent;

reversing the pH gradient perfusing the cation exchange adsorbent to develop from a predetermined minimum pH to a predetermined first maximum pH at the temperature $T_1$;

collecting the charged molecules, each of which separately elutes from the cation exchange adsorbent at its effective isoelectric point, until the predetermined first maximum pH is reached at the temperature $T_1$;

changing the temperature of the cation exchange resin to $T_2$;

continuing to perfuse the cation exchange adsorbent with a pH gradient that is increasing in time from the predetermined first maximum pH to a predetermined second maximum pH at the temperature $T_2$;

collecting the charged molecules, each of which separately elutes from the cation exchange adsorbent at its effective isoelectric point, until the predetermined second maximum pH is reached at the temperature $T_2$;

repeating a stepwise change in temperature followed by elution using a pH gradient that is increasing and collecting the charged molecules, each of which separately elutes from the cation exchange adsorbent in time, until a final temperature, $T_f$, is reached;

continuing perfusion of the cation exchange adsorbent with a pH gradient that is increasing in time from a predetermined penultimate maximum pH to a predetermined ultimate maximum pH; and collecting the charged molecules, each of which separately elutes from the cation exchange adsorbent at its effective isoelectric point until the ultimate maximum pH is reached at the final temperature, $T_f$.

In another aspect of the invention, there is provided a combined external gradient chromatofocusing method of chromatographically separating charged molecules having different isoelectric points, comprising:

applying and binding the charged molecules to be separated to a cation exchange adsorbent perfused with a solvent comprising at least one buffering component at an initial minimum pH and at a temperature $T_0$ where the cation exchange adsorbent has a charge opposite that of the charged molecules;

connecting an anion exchange adsorbent in series after the cation exchange adsorbent, changing the temperature of the anion exchange adsorbent to $T_1$ and equilibrating both exchangers at the initial minimum pH as measured at the temperature $T_0$;

supplying to the cation exchange adsorbent an eluent at the temperature $T_0$ with a time dependent pH formed from the continuous mixing of a solution at the initial pH containing the at least one buffering component pumped out from a first reservoir with a solution at a different pH containing the at least one buffering component pumped out from a second reservoir, wherein the mixing proportions vary to maintain an unretained pH gradient with an externally defined slope;

eluting the charged molecules, each of which separately elutes from the cation exchange adsorbent at its effective isoelectric point, until a predetermined maximum pH is reached at the temperature $T_0$;

directing the resulting effluent from the cation exchange adsorbent containing the charged molecules into the anion exchange adsorbent to be further separated at the temperature $T_1$;

binding the charged molecules that are negatively charged to the anion exchange adsorbent until the predetermined maximum pH is reached at the temperature $T_0$;

removing the cation exchange adsorbent, reversing the pH gradient perfusing the anion exchange adsorbent to develop from a predetermined maximum pH to a predetermined first minimum pH at the temperature $T_1$;

collecting the charged molecules, each of which separately elutes from the anion exchange adsorbent at its effective isoelectric point, until the predetermined first minimum pH is reached at the temperature $T_1$;

changing the temperature of the anion exchange resin to $T_2$;

continuing to perfuse the anion exchange adsorbent with a pH gradient that is decreasing in time from the predetermined first minimum pH to a predetermined second minimum pH at the temperature $T_2$;

collecting the charged molecules, each of which separately elutes from the anion exchange adsorbent at its effective isoelectric point, until the predetermined second minimum pH is reached at the temperature $T_2$;

repeating the stepwise change in temperature followed by elution using a pH gradient that is increasing and collecting the charged molecules, each of which separately elutes from the anion exchanger in time, until a final temperature, $T_f$, is reached;

continuing perfusion of the anion exchange adsorbent with a pH gradient that is decreasing in time from a predetermined penultimate minimum pH to a predetermined ultimate minimum pH; and collecting the charged molecules, each of which separately elutes from the anion exchange adsorbent at its effective isoelectric point, until the ultimate minimum pH is reached at the final temperature, $T_f$.

In another aspect of the invention, there is provided a combined external gradient chromatofocusing method of chromatographically separating charged molecules having different isoelectric points, comprising:

applying the charged molecules to be separated to an anion exchange adsorbent at a temperature $T_0$, which is followed by a cation exchange adsorbent connected in a series at a temperature $T_1$, such that the two adsorbents are perfused with a solvent comprising at least one buffering component at an initial pH as measured at the temperature $T_0$ where the charged molecules to be separated fall into at least one of the three charge classes: negatively charged for those charged molecules that have apparent pIs below the initial pH; neutral for those charged molecules that fail to bind to either the anion exchange adsorbent or the cation exchange adsorbent at the initial pH; and positively charged for those charged molecules that have apparent pIs above the initial pH;

binding the charged molecules which are negatively charged at the initial pH to the anion adsorbent at the temperature $T_0$;

binding the charged molecules which are positively charged at the initial pH to the cation adsorbent at the temperature $T_1$;

collecting those charged molecules which fail to bind to either the anion exchange adsorbent at the temperature $T_0$ or the cation exchange adsorbent at the temperature $T_1$ at the initial pH;

disconnecting the cation exchange adsorbent and anion exchange adsorbent from each other at the initial pH;

supplying to the anion exchange adsorbent an eluent with a time dependent decreasing pH starting at the initial pH as measured at the temperature $T_0$ formed from the continuous mixing of a solution at the initial pH containing the at least one buffering component pumped out from a first reservoir with a solution at a different pH containing the at least one buffering component pumped out from a second reservoir, wherein the mixing proportions vary to maintain an unretained pH gradient with an externally defined slope at the temperature $T_0$;

collecting the charged molecules, each of which separately elutes from the anion exchange adsorbent at its effective isoelectric point, until a final minimum pH is reached at the temperature $T_0$;

supplying to the cation exchange adsorbent an eluent with a time dependent increasing pH starting at an initial pH as measured at the temperature $T_1$ formed from the continuous mixing of a solution at the initial pH containing the at least one buffering component pumped out from a first reservoir with a solution at a different pH containing the at least one buffering component pumped out from a second reservoir, wherein the mixing proportions vary to maintain an unretained pH gradient with an externally defined slope at the temperature $T_1$; and collecting the charged molecules, each of which separately elutes from the cation exchange adsorbent at its effective isoelectric point until a final maximum pH is reached at the temperature $T_1$.

In another aspect of the invention, there is provided a combined external gradient chromatofocusing method of chromatographically separating charged molecules having different isoelectric points, comprising:

applying the charged molecules to be separated to a cation exchange adsorbent at a temperature $T_0$, which is followed by an anion exchange adsorbent connected in a series at a temperature $T_1$, such that the two adsorbents are perfused with a solvent comprising at least one buffering component at an initial pH as measured at the temperature $T_0$ where the charged molecules to be separated fall into one of the three charge classes: negatively charged for those charged molecules that have apparent pIs below the initial pH; neutral for those charged molecules that fail to bind to either the anion exchange adsorbent or the cation exchange adsorbent at the initial pH; and positively charged for those charged molecules that have apparent pIs above the initial pH;

binding the charged molecules which are positively charged at the initial pH to the cation adsorbent at the temperature $T_0$;

binding the charged molecules which are negatively charged at the initial pH to the anion adsorbent at the temperature $T_1$;

collecting those charged molecules which fail to bind to either the anion exchange adsorbent at the temperature $T_0$ or the cation exchange adsorbent at the temperature $T_1$ at the initial pH;

disconnecting the cation exchange adsorbent and anion exchange adsorbent from each other at the initial pH;

supplying to the cation exchange adsorbent an eluent with a time dependent increasing pH starting at the initial pH as measured at the temperature $T_0$ formed from the continuous mixing of a solution at the initial pH containing the at least one buffering component pumped out from a first reservoir with a solution at a different pH containing the at least one buffering component pumped out from a second reservoir, wherein the mixing proportions vary to maintain an unretained pH gradient with an externally defined slope at the temperature $T_0$;

collecting the charged molecules, each of which separately elutes from the cation exchange adsorbent at its effective isoelectric point until a final maximum pH is reached at the temperature $T_0$;

supplying to the anion exchange adsorbent an eluent with a time dependent decreasing pH starting at an initial pH as measured at the temperature $T_1$ formed from the continuous mixing of a solution at the initial pH containing the at least one buffering component pumped out from a first reservoir with a solution at a different pH containing the at least one buffering component pumped out from a second reservoir, wherein the mixing proportions vary to maintain an unretained pH gradient with an externally defined slope at the temperature $T_1$; and collecting the charged molecules, each of which separately elutes from the anion exchange adsorbent at its effective isoelectric point, until a final minimum pH is reached at the temperature $T_1$.

In another aspect of the invention, there is provided a combined external gradient chromatofocusing method of chromatographically separating charged molecules having different isoelectric points, comprising:

applying and binding the charged molecules to be separated to an anion exchange adsorbent perfused with a solvent comprising at least one buffering component at an initial maximum pH measured at a temperature $T_0$ where the anion exchange adsorbent has a charge opposite that of the charged molecules wherein the anion exchange adsorbent is subjected to a temperature gradient from a temperature $T_1$ to a temperature $T_2$ wherein the temperature $T_1$ is the temperature of the adsorbent where the solvent enters the adsorbent and the temperature $T_2$ is the temperature where the solvent exits the adsorbent;

connecting in series after the anion exchange adsorbent a cation exchange adsorbent subjected to a temperature gradient from a temperature $T_3$ to a temperature $T_4$ wherein the temperature $T_3$ is the temperature of the cation exchange adsorbent where the effluent from the anion exchange adsorbent enters the cation exchanger and the temperature $T_4$ is the temperature where the effluent exits the cation exchanger and equilibrating both exchangers at the initial maximum pH as measured at the temperature $T_0$;

supplying to the anion exchange adsorbent, subjected to the temperature gradient from the temperature $T_1$ to the temperature $T_2$, an eluent with a time dependent pH formed from the continuous mixing of a solution at the initial pH containing the at least one buffering component pumped out from a first reservoir at the temperature $T_0$ with a solution at a different pH containing the at least one buffering component pumped out from a second reservoir at the temperature $T_0$, wherein the mixing proportions vary to maintain an unretained pH gradient with an externally defined slope;

eluting the charged molecules, each of which separately elutes from the anion exchange adsorbent at its effective isoelectric point, until a predetermined minimum pH is reached as measured at the temperature $T_0$;

directing the resulting effluent from the anion exchange adsorbent containing the charged molecules into the cation exchange adsorbent subjected to the temperature gradient from the temperature $T_3$ to the temperature $T_4$ to be further separated;

binding the charged molecules that are positively charged to the cation exchange adsorbent subjected to the temperature gradient from the temperature $T_3$ to the temperature $T_4$ until the predetermined minimum pH is reached as measured at the temperature $T_0$;

removing the anion exchange adsorbent;

reversing the pH gradient perfusing the cation exchange adsorbent subjected to the temperature gradient from the temperature $T_3$ to the temperature $T_4$ to develop from a predetermined minimum pH to a predetermined maximum pH as measured at the temperature $T_0$ and;

collecting the charged molecules, each of which separately elutes from the cation exchange adsorbent subjected to the temperature gradient from the temperature $T_3$ to the temperature $T_4$ at its effective isoelectric point, until the predetermined maximum pH is reached as measured at the temperature $T_0$.

In another aspect of the invention, there is provided a combined external gradient chromatofocusing method of chromatographically separating charged molecules having different isoelectric points, comprising:

applying and binding the charged molecules to be separated to a cation exchange adsorbent perfused with a solvent comprising at least one buffering component at an initial minimum pH measured at a temperature $T_0$ where the cation exchange adsorbent has a charge opposite that of the charged molecules wherein the cation exchange adsorbent is subjected to a temperature gradient from a temperature $T_1$ to a temperature $T_2$ wherein the temperature $T_1$ is the temperature of the adsorbent where the solvent enters the adsorbent and the temperature $T_2$ is the temperature where the solvent exits the adsorbent;

connecting in series after the cation exchange adsorbent an anion exchange adsorbent subjected to a temperature gradient from a temperature $T_3$ to a temperature $T_4$ wherein the temperature $T_3$ is the temperature of the anion exchange adsorbent where the effluent from the cation exchange adsorbent enters the anion exchanger and the temperature $T_4$ is the temperature where the effluent exits the anion exchanger and equilibrating both exchangers at the initial minimum pH as measured at the temperature $T_0$;

supplying to the cation exchange adsorbent, subjected to the temperature gradient from the temperature $T_1$ to the temperature $T_2$, an eluent with a time dependent pH formed from the continuous mixing of a solution at the initial pH containing the at least one buffering component pumped out from a first reservoir at the temperature $T_0$ with a solution at a different pH containing the at least one buffering component pumped out from a second reservoir at the temperature $T_0$, wherein the mixing proportions vary to maintain an unretained pH gradient with an externally defined slope;

eluting the charged molecules, each of which separately elutes from the cation exchange adsorbent at its effective isoelectric point, until a predetermined maximum pH is reached as measured at the temperature $T_0$;

directing the resulting effluent from the cation exchange adsorbent containing the charged molecules into the anion exchange adsorbent subjected to the temperature gradient from the temperature $T_3$ to the temperature $T_4$ to be further separated;

binding the charged molecules that are negatively charged to the anion exchange adsorbent subjected to the temperature gradient from the temperature $T_3$ to the temperature $T_4$ until the predetermined maximum pH is reached as measured at the temperature $T_0$;

removing the cation exchange adsorbent;

reversing the pH gradient perfusing the anion exchange adsorbent subjected to the temperature gradient from the temperature $T_3$ to the temperature $T_4$ to develop from a predetermined maximum pH to a predetermined minimum pH as measured at the temperature $T_0$ and;

collecting the charged molecules, each of which separately elutes from the anion exchange adsorbent subjected to the temperature gradient from temperature $T_3$ to temperature $T_4$ at its effective isoelectric point, until the predetermined minimum pH is reached as measured at the temperature $T_0$.

A further aspect of the invention is a buffering composition for chromatographically separating on an ion exchange resin charged molecules having different isoelectric points, comprising an aqueous solution of at least three buffering components such that when the composition at a predetermined pH is titrated with the composition at a different predetermined pH, the change in the pH of the mixture of the two compositions will be directly linearly proportional to the fraction of the mixture represented by each of the two compositions.

Another aspect of the invention is a chromatographic system for separating charged molecules comprising:

a column containing an ion exchange adsorbent perfused with a solvent comprising at least three buffering components at an initial pH, wherein the ion exchange adsorbent has a charge opposite that of the charged molecules to be separated;

a first reservoir containing a first solution comprising the at least three buffering components at the initial pH;

a second reservoir containing a second solution comprising the at least three buffering components at a pH different from the initial pH; and a means of delivering an externally created mixture of the first and second solutions so as to form an externally defined pH gradient to the adsorbent and produce an unretained pH gradient within the column.

Another aspect of the invention is a chromatographic system for separating charged molecules comprising:

a column containing an ion exchange adsorbent perfused with a solvent comprising at least three buffering components at an initial pH, wherein the ion exchange adsorbent has a charge opposite that of the charged molecules to be separated;

a first reservoir containing a first solution comprising the at least three buffering components at the initial pH, with or without additional buffering components;

a second reservoir containing a second solution comprising the at least three buffering components at a pH different from the initial pH, with or without additional buffering components; and a means of delivering an externally created mixture of the first and second solutions so as to form an externally defined pH gradient from the initial pH to the final pH and produce an unretained pH gradient within the column.

Another aspect of the invention comprises a feedback controlling system for automatically correcting pH deviations in a preprogrammed time dependent pH gradient generated by a chromatographic system comprising:

a pH measuring device that produces an output voltage that is a known function of the measured pH; and a feedback controller that receives as an input at appropriately short time intervals a voltage from the pH measuring device that monitors the pH of the eluent as generated by the chromatographic system and compares that voltage to a set-point voltage corresponding to an expected pH value of a preprogrammed time dependent pH gradient;

calculates a difference, the absolute value of which is referred to as the error, between the input voltage (i.e. measured pH) and the set-point voltage (i.e. expected pH); and adjusts the pumping rate of the gradient-generating pumps of the chromatographic system using any known feedback algorithms for calculating a correction signal, either as current or voltage as is appropriate, such that the absolute value of the error is minimized.

Yet another aspect of the invention is a chromatographic system for separating charged molecules and for producing an adjusted unretained pH gradient within a column, comprising:

a column containing an ion exchange adsorbent perfused with a solvent comprising at least one buffering component at an initial pH, wherein the ion exchange adsorbent has a charge opposite that of the charged molecules to be separated;

a first reservoir containing a first solution comprising the at least one buffering component at the initial pH;

a second reservoir containing a second solution comprising the at least one buffering component at a pH different from the initial pH;

a first reservoir pump and a second reservoir pump for mixing the first and second solutions such that the pumping rates of the first reservoir pump and the second reservoir pump are adjusted so as to form an externally defined elution pH gradient at a controlled flow rate; and a feedback controlling system as described above for monitoring and correcting the formation of the externally defined elution pH gradient at the controlled flow rate, wherein the pH measuring device is a pH flow cell.

In another aspect of the invention, there is provided a chromatofocusing method of chromatographically separating charged molecules having different isoelectric points, comprising:

adding the charged molecules to be separated to an anion exchange adsorbent perfused with a solvent comprising at least one buffering component at an initial maximum pH where the anion exchange adsorbent has a charge opposite that of the charged molecules to be separated;

supplying to the anion exchange adsorbent an eluent with a time dependent pH formed from the continuous mixing of a solution at the initial pH containing the at least one buffering component with or without additional buffering components pumped out from a first reservoir with a solution at a different pH containing the at least one buffering component with or without additional buffering components pumped out from a second reservoir into a mixer;

flowing the eluent from the mixer through a pH flow cell wherein a pH dependent voltage signal is generated, allowing the proportions of the solutions pumped from the first reservoir and the second reservoir to be varied by the feedback controlling system discussed above such that an unretained pH gradient with an externally defined and adjusted slope is maintained; and collecting the charged molecules, each of which separately elutes from the anion exchange adsorbent at its effective isoelectric point.

In another aspect of the invention, there is provided a reverse chromatofocusing method of chromatographically separating charged molecules having different isoelectric points, comprising:

adding the charged molecules to be separated to an cation exchange adsorbent perfused with a solvent comprising at least one buffering component at an initial minimum pH where the cation exchange adsorbent has a charge opposite that of the charged molecules to be separated;

supplying to the cation exchange adsorbent an eluent with a time dependent pH formed from the continuous mixing of a solution at the initial pH containing the at least one buffering component with or without additional buffering components pumped out from a first reservoir with a solution at a different pH containing the at least one buffering component with or without additional buffering components pumped out from a second reservoir into a mixer;

flowing the eluent from the mixer through a pH flow cell wherein a pH dependent voltage signal is generated allowing the proportions of solutions pumped from the first reservoir and the second reservoir to be varied by the feedback controlling system discussed above such that an unretained pH gradient with an externally defined and adjusted slope is maintained; and collecting the charged molecules, each of which separately elutes from the cation exchange adsorbent at its effective isoelectric point.

Yet another aspect of the invention is a chromatographic system for separating charged molecules and for producing an adjusted unretained pH gradient within a column, comprising:

a column containing an ion exchange adsorbent perfused with a solvent comprising at least one buffering component at an initial pH, wherein the ion exchange adsorbent has a charge opposite that of the charged molecules to be separated;

a first reservoir containing a first solution comprising the at least one buffering component at the initial pH;

a second reservoir containing a second solution comprising the at least one buffering component at a pH different from the initial pH;

a first reservoir pump and a second reservoir pump for pumping the first and second solutions into a mixing chamber containing a predetermined volume of the first solution such that the pumping rates of the first reservoir pump and the second reservoir pump are adjusted so as to form an externally defined elution pH gradient at a controlled flow rate;

a feedback controlling system as described above for monitoring and correcting the formation of the externally defined elution pH gradient at the controlled flow rate, wherein the pH measuring device is a pH electrode immersed in the mixing chamber; and a means for pumping the mixed solutions out of the mixing chamber at the controlled flow rate.

In another aspect of the invention, there is provided a chromatofocusing method of chromatographically separating charged molecules having different isoelectric points, comprising:

adding the charged molecules to be separated to an anion exchange adsorbent perfused with a solvent containing at least one buffering component at an initial maximum pH where the anion exchange adsorbent has a charge opposite that of the charged molecules to be separated;

supplying to the anion exchange adsorbent an eluent with a time dependent pH formed from the continuous mixing of a solution containing the at least one buffering component at the initial pH pumped out from a first reservoir with a solution at a different pH containing the at least one buffering component pumped out from a second reservoir into a mixing chamber;

measuring the pH of the eluent by a means of a pH electrode immersed in the mixing chamber that generates a pH dependent voltage signal;

correcting the pumping rate of the solution delivered from the first reservoir and the pumping rate of the solution delivered from the second reservoir by utilizing the voltage signal from the pH electrode and the above discussed feedback controlling system such that an unretained pH gradient with an externally defined and adjusted slope is maintained;

delivering the eluent from the mixing chamber through the column containing the anion exchange adsorbent; and collecting the charged molecules, each of which separately elutes from the anion exchange adsorbent at its effective isoelectric point.

In another aspect of the invention, there is provided a reverse chromatofocusing method of chromatographically separating charged molecules having different isoelectric points, comprising:

adding the charged molecules to be separated to a cation exchange adsorbent perfused with a solvent comprising at least one buffering component at an initial minimum pH where the cation exchange adsorbent has a charge opposite that of the charged molecules to be separated;

supplying to the cation exchange adsorbent an eluent with a time dependent pH formed from the continuous mixing of a solution containing the at least one buffering component at the initial pH pumped out from a first reservoir with a solution at a different pH containing the at least one buffering component pumped out from a second reservoir into a mixing chamber;

measuring the pH of the eluent by a means of a pH electrode immersed in the mixing chamber that generates a pH dependent voltage signal;

correcting the pumping rate of the solution delivered from the first reservoir and the pumping rate of the solution delivered from the second reservoir by utilizing the voltage signal from the pH electrode and a feedback controlling system such that an unretained pH gradient with an externally defined and adjusted slope is maintained;

delivering the eluent through the column containing the cation exchange adsorbent; and collecting the charged molecules, each of which separately elutes from the cation exchange adsorbent at its effective isoelectric point.

Although the present invention is broadly as defined above, it will be appreciated by those person skilled in the art that it is not limited thereto and that it further includes the aspects which are described below.

Further objects and advantages of the present invention will be clear from the description that follows.

BRIEF DESCRIPTION OF THE DRAWINGS

The appended drawings have been included herein so that the above recited features, advantages and objects of the invention can be understood in detail. These drawings form a part of the specification. However, it is to be noted that the appended drawings illustrate preferred aspects of the invention and should not be considered to limit the scope of the invention as described herein.

FIG. 1, panel A. Mixture of Myoglobin, Phosphoglycerate kinase (PGK) Conalbumin, Conalbumin Iron complex, Human Transferin (HT), β-lactoglobulin (β1g) and Soybean Trypsin Inhibitor (STI) dissolved in 5 mM Methyl Piperazine, 5 mM Piperazine, 5 mM Triethanolamine (TE) buffer pH 9.5, bound to Mono Q HR 5/5 column at pH 9.5, separated by external gradient chromatofocusing.

FIG. 1, panel B. Effluent pH profile (dotted line) observed during elution of Mono Q HR 5/5 by external pH gradient generated upon mixing of 5 mM Methyl Piperazine, 5 mM Piperazine, 5 mM TE buffer pH 9.5 with 5 mM Methyl Piperazine, 5 mM Piperazine, 5 mM TE buffer pH 3.5. Mono Q HR 5/5 was equilibrated with 5 mM Methyl Piperazine, 5 mM Piperazine, 5 mM TE buffer pH 9.5. Flow rate 1 ml/min, length of pH gradient formation from pH 9.5 to pH 3.5 40 column volumes.

FIG. 2, panel A. Mixture of Myoglobin, PGK, Conalbumin, Conalbumin iron complex, Human Transferin, β1g and Soybean Trypsin Inhibitor dissolved in a 4 mM Bis-Tris Propane, 4 mM Methyl Piperazine, 4 mM Piperazine, 4 mM TE buffer pH 9.5, bound to Mono Q HR 5/5 column at pH 9.5, separated by external gradient chromatofocusing.

FIG. 2, panel B. Effluent pH profile (dotted line) observed during elution of Mono Q HR 5/5 by external pH gradient generated upon mixing 4 mM Bis-Tris Propane, 4 mM Methyl Piperazine, 4 mM Piperazine, 4 mM TE buffer pH 9.5 with 4 mM Bis-Tris Propane, 4 mM Methyl Piperazine, 4 mM Piperazine, 4 mM TE buffer pH 3.5. Mono Q HR 5/5 was equilibrated with 4 mM Bis-Tris Propane, 4 mM Methyl Piperazine, 4 mM Piperazine, 4 mM TE buffer pH 9.5. Flow rate 1 ml/min, length of gradient formation (elution) from pH 9.5 to pH 3.5 40 column volumes.

FIG. 3, panel A. Retained pH gradient chromatofocusing separation of PGK employing the commercially marketed chromatofocusing system by Pharmacia—a weak anionic exchanger column, Mono P HR 5/20, and Polybuffers—starting buffer 25 mM TE, iminodiacetic acid pH 8.3, elution buffer 6 ml Polybuffer 96+14 ml Polybuffer 74, iminodiacetic acid pH 5 diluted to 200 ml. Flow rate 1 ml/min, length of elution with Polybuffer 12 column volumes. Note the small separation between peaks.

FIG. 3, panel B. PGK separated using a simple two component buffer system 5 mM Piperazine, 5 mM TE and the Mono P HR 5/20 showing that a separation can be achieved by hybrid (external plus retained internal gradient) chromatofocusing on a weak anionic exchanger without using Polybuffers. Flow rate 1 ml/min, length of elution with external pH gradient 18 column volumes.

FIG. 3, panel C. PGK separated by external gradient chromatofocusing using the same two component buffer system as in Example 3, panel B but on the strong anionic exchanger Mono Q HR 5/5 showing better linear pH profile (dotted line). Flow rate 1 ml/min, length of elution with external linear pH gradient 35 column volumes.

FIG. 3, panel D. External pH gradient chromatofocusing of PGK separated on Mono Q HR 5/5 using the present invention's four component buffer shown in Example 2. Flow rate 1 ml/min, length of gradient formation 20 column volumes. Note the extremely linear pH gradient of the effluent (dotted line) and the resulting best separation of the protein species.

FIG. 4, panel A. Mixture of Soybean Trypsin Inhibitor, β1g, Human Transferin and Conalbumin dissolved in 4 mM Bis-Tris Propane, 4 mM Methyl Piperazine, 4 mM Piperazine, 4 mM TE buffer pH 4, bound to Mono S HR 5/5 column at pH 4, separated by external gradient reverse chromatofocusing.

FIG. 4. panel B. Effluent pH profile (dotted line) observed during elution of Mono S HR 5/5 by external pH gradient generated upon mixing 4 mM Bis-Tris Propane, 4 mM Methyl Piperazine, 4 mM Piperazine, 4 mM TE buffer pH 4 with 4 mM Bis-Tris Propane, 4 mM Methyl Piperazine, 4 mM Piperazine, 4 mM TE buffer pH 9.5. Mono S HR 5/5 was equilibrated with 4 mM Bis-Tris Propane, 4 mM Methyl Piperazine, 4 mM Piperazine, 4 mM TE buffer pH 4. Flow rate 1 ml/min, length of elution with external linear pH gradient from pH 4 to pH 9.5 37 column volumes.

FIG. 5, panel A. Effluent pH and absorbance profiles (curves 1, 2) during chromatofocusing on Mono Q HR 5/5 and reverse chromatofocusing on Mono S HR 5/5 (curves 3, 4) utilizing the wide pH range buffering system.

FIG. 5, panel B. Concentration traces of the preprogrammed external gradient formation and actual gradient development reflected by the effluent conductivity upon chromatofocusing on Mono Q HR 5/5 (curves 1, 2) and reverse chromatofocusing on Mono S HR 5/5 (curves 3, 4) utilizing the wide pH range buffering system.

FIG. 6, Panel A. A chromatographic system utilizing a pH flow cell as a feedback source sending a pH dependent voltage signal to a feedback controller that corrects the formation of the pH gradient when necessary.

FIG. 6, Panel B. A chromatographic system utilizing a pH electrode in a mixing chamber as a feedback source sending a pH dependent voltage signal to a feedback controller that corrects the formation of the pH gradient when necessary. The eluent with a time dependent pH is pumped out from the mixing chamber to an ion exchange column by an additional pump.

DETAILED DESCRIPTION OF THE INVENTION

Figure 1:
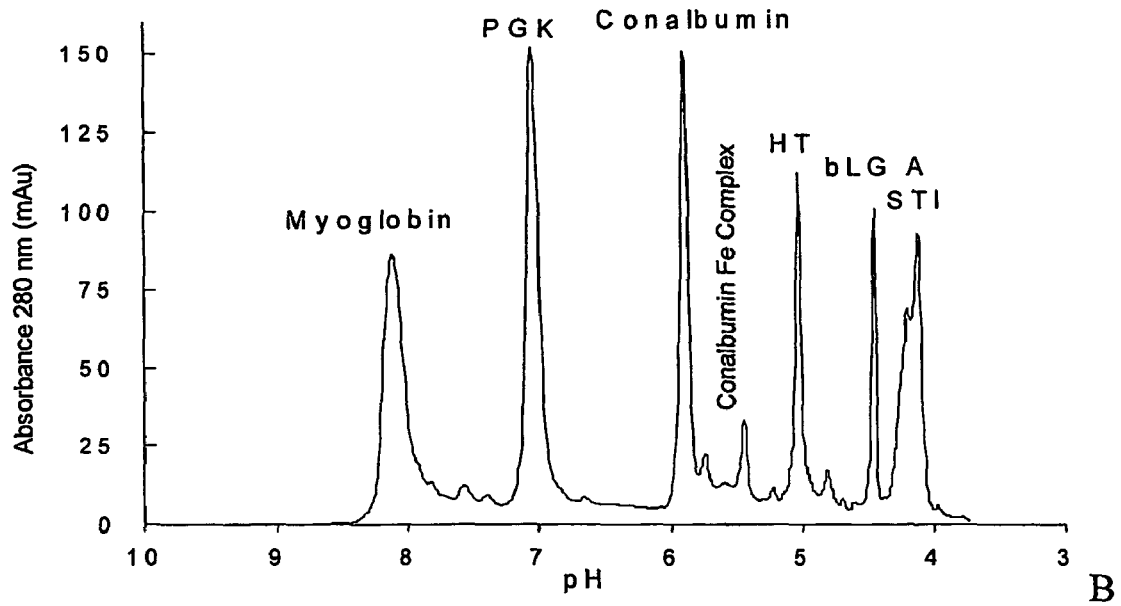
FIG. 1. This figure depicts the separation of a complex mixture of proteins by external gradient chromatofocusing on a strong anion exchange column using a 3-component buffer system.
Figure 1:
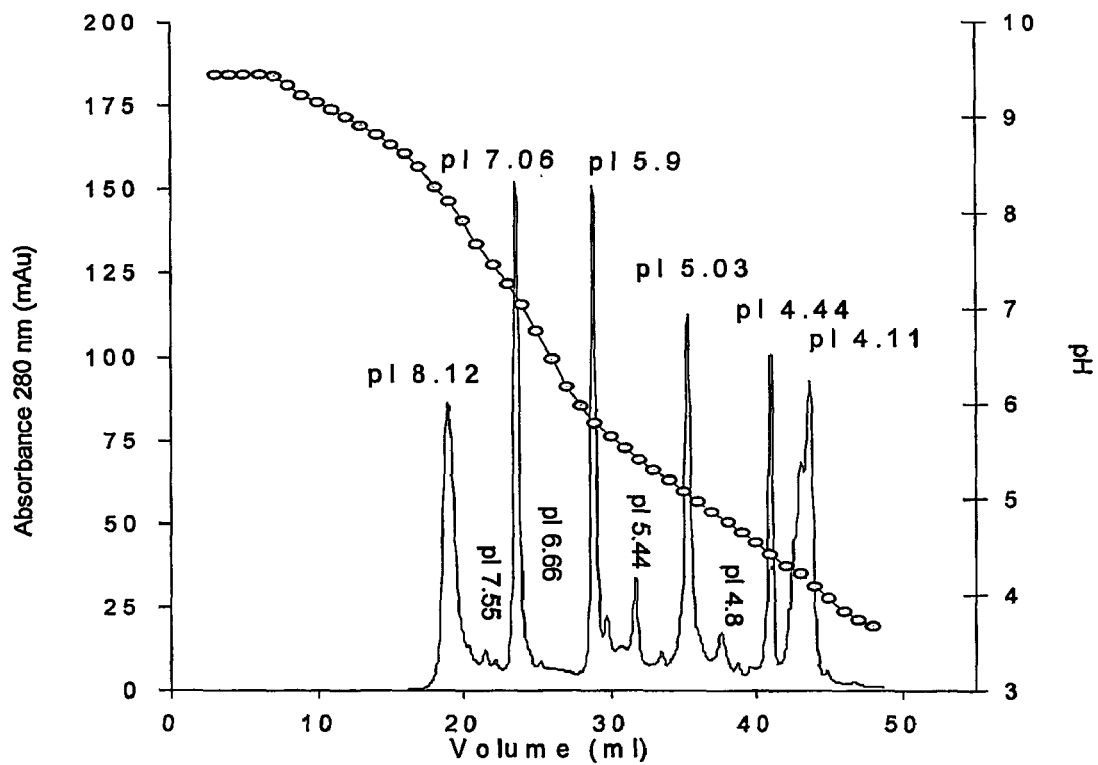

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, the term "chromatographic column" or "column" refers to a tube packed with adsorbent particles and used to perform chromatography.

As used herein, the term "resin" or "adsorbent" or "exchanger" refers to the solid material inside the chromatographic column which selectively binds (i.e. adsorbs) one or more of the charged species to be separated. The adsorbent will be either an anionic exchanger or a cationic exchanger.

As used herein, the term "ampholyte" refers to a molecule containing groups with both acidic and basic pKa values. Ampholytes with more than two charged groups are called polyampholytes.

As used herein, the term "anionic exchange adsorbent" refers to an adsorbent that is positively charged and binds anions (i.e. negatively charged species).

As used herein, the term "cationic exchange adsorbent" refers to an adsorbent that is negatively charged and binds cations (i.e. positively charged species).

As used herein, the term "ion exchange adsorbent" includes both anionic exchange adsorbent and cationic exchange adsorbent.

As used herein, the term "unretained pH gradient" refers to the existing internal column pH gradient from the top to the bottom of the column due to the fact that the column has a length. In the external gradient chromatofocusing (reverse chromatofocusing) the external pH gradient evolves in time from the initial pH towards the final pH so that the pH at the bottom of the column is closer to the initial pH than the pH at the top of the column. Typically, in the other reported chromatofocusing techniques, the retained pH gradient refers to the internal column gradient created due to the differential binding of the Polybuffer species or other buffer species to the weak anion or cation exchanger through the length of the column.

As used herein, the term "externally defined slope" means that the slope of the pH gradient is externally defined because it is generated by the computer controlled mixing of two external buffers at different pHs. The rate at which the pH will change (i.e. the slope of pH gradient) depends exclusively on the operator and it is virtually independent of the column properties, especially when strong ion exchanging resins are used. These resins do not change their (properties) charge over their entire working pH range. In contrast, when weak ion exchanging resins are used, the slope will depend somewhat on the properties of the column as in the case of the classical chromatofocusing described by Sluyterman or in chromatofocusing procedures described by Frey and Logan.

The chromatographic systems that have been developed, external gradient chromatofocusing ("ExGC") and reverse external gradient chromatofocusing ("RevExGC"), are fundamentally different from known systems in several key ways. For one, a unique combination of common, inexpensive, buffering compounds with widely spaced but overlapping $pK_a$'s wherein the molar proportion of each component remains constant or varies throughout the transition between the initial pH and the final pH is employed to achieve an unprecedented breadth of nearly linear pH gradients on strong anionic and cationic columns over ranges from pH 2 to 12 or broader (depending on a column's pH stability properties). This range is more than twice the largest reported pH range (4.5 units, Logan et al., *Biotechnology and Bioengineering*, 62(2), 1999). Similar to established variations of chromatofocusing, the invention also works well over very narrow pH ranges (e.g. 0.1 pH unit) and when this capability is combined with a change of column temperature, even proteins exhibiting virtually identical pI's at an initial temperature can be separated, for example, in a second chromatofocusing purification step at a different temperature.

Another advantage of the invention over known methods is that the initial and final pH values of the gradient are limited only either by the pH range of the buffer composition or by the recommended stable working pH range of the strong exchanger resin. While the invention performs reliably on both strong and weak anionic and cationic columns, strong anionic and cationic columns are preferred aspects. FIGS. 1-5 demonstrate the versatility of the methods of the invention between pH 2.5 and 10.5 as well as at narrower ranges, but commonly available buffers allow the creation of nearly linear gradients in this system over the full working range of strong anionic and cationic resins which could be from pH 0 to 14. However, this near linearity of the pH gradient would still be very difficult to achieve without the use of a solely externally generated gradient.

This gradient-forming method represents another major difference between the methodology of the invention and the known retained gradient technologies. The external gradient is generated by the continuous mixing of a starting pH buffer with a second buffer at a different pH, simultaneously increasing the proportion of the second buffer until the mixture reaches the desired pH. Each of the pH gradient forming buffer solutions can consist of either the same buffering components or different buffering components. The gradient can be linear or nonlinear (i.e. concave or convex or stepwise) in shape. In preferred aspects, the column is a strong anionic or strong cationic exchange column, which means that the column adsorbent's ion exchange properties do not change over the working pH range of the column.

Despite the fact that the charged groups of the column adsorbent do not control the pH profile, the focusing capability of the method of the invention is as good as or better than systems described in the literature. The conditions that produce focusing in the invention are analogous to those in the published systems but with some important differences. For example, suppose a strong anionic exchange column has been pre-equilibrated to an alkaline pH of choice and then a mixture of proteins is allowed to bind at the top of the column. In the process of separation, when the pH of the elution buffer reaches the pI of a particular protein, the protein ceases to bind strongly to the column and begins to descend through the column in an initially sharp band. If no focusing forces were present, this band would become more diffuse as it descended in the column due to ordinary diffusion away from the center of motion of the band. However, the pH of the buffer in the column below the elution front is progressively more alkaline with increasing distance below the front, while the buffer above is progressively more acidic with increasing distance above the front just as in the case of a retained gradient formed by differential binding of complex buffer species (i.e. Polybuffers) to a weak anionic column. Thus, just as in those reported systems, protein molecules lagging behind the elution front become more positively charged the longer they lag because of the increasingly acidic buffer with the result that these protein molecules are increasingly accelerated by repulsion from the like charges of the column adsorbent. Conversely, protein molecules diffusing ahead of the elution front carry a greater negative charge the further ahead they are (due to the more alkaline downfront pH) and thus are slowed by increased binding to the opposite charges of the column adsorbent. As a result of this process, the protein band is continuously refocused, retains its sharpness and exits the column as a narrow band.

Although the refocusing forces are similar in the two systems the external gradient chromatofocusing of the invention differs in two important aspects. First, the pH gradient along the length of the column, unlike that of the Polybuffer system, is a consequence of the fact that fluid lower down in the column entered earlier in time and therefore at a pH closer to the initial pH. Thus the longer the column the greater the pH difference between top and bottom. This effect is intensified somewhat by simple bulk fluid mixing of the front with the column fluid below it which tends to increase the gradient. In general, the range of the pH gradient from the top of the column to the bottom of the column at any given time will be much narrower than the difference in pH between the pH of starting buffer and the pH of the final buffer, i.e. the pH range over which the separation is conducted. Second, the column pH gradient is independent of the range of the gradient in time so there is no tradeoff between optimizing spatial gradient conditions for the best possible separation and the range of pH over which this separation can be achieved. In contrast, in the internally generated gradient systems, the larger the range of pH used for separation, the steeper the spatial column gradient and the more compromised the separation becomes. In addition, the external gradient chromatofocusing system creates a sharp elution band as soon as the protein is released from the column, whereas the internal gradient systems start focusing the eluting protein band only when the protein reaches its pI within the retained pH gradient.

The ability to construct external linear gradients over wide pH ranges using either chromatofocusing or reverse chromatofocusing confers unique preparative power to this technique. One example would be a purification of several low abundance proteins from a mixture such as avian egg white containing large quantities of ovalbumin. The ovalbumin protein has a pI of 4.6. Using the method of the invention on a strong cationic column such as Mono S, one could initially equilibrate the column to pH 4.6, apply the sample, wash the column with the initial buffer and then elute to the final required pH. This reverse chromatofocusing approach allows the vast bulk of ovalbumin to pass through the column without binding during the sample application and initial isocratic wash, thus increasing the binding efficiency of all proteins with pI's>4.7. This selective and quick separation of ovalbumin and proteins with pI's<4.6 from proteins with pI's>4.6 would not be possible if a standard chromatofocusing protocol had been used.

Another advantage of both the external gradient chromatofocusing and reverse chromatofocusing system are variants we term heterothermal external gradient chromatofocusing, heterothermal reverse external gradient chromatofocusing, isothermal shift external gradient chromatofocusing and isothermal shift reverse external gradient chromatofocusing. The heterothermal variation of the basic technique involves applying a significant temperature gradient from the top to the bottom of the exchange column either before loading the charged molecules to be separated or subsequent to loading the charged molecules to be separated. The isothermal shift variation of the basic technique involves changing the column temperature uniformly along its length from an initial temperature to a final temperature either before loading the charged molecules to be separated or subsequent to loading the charged molecules to be separated.

The advantage conferred by these two thermal techniques is related to the fact that the $pK_a$'s of the buffers and the pI's of the eluted proteins are shifted while traversing the column. A temperature gradient or shift will therefore allow the separation of protein species exhibiting virtually identical pI's at a given temperature due to different changes in their pI's as the temperature is shifted away from that given temperature since the total charge of the various proteins is generally determined from their different charged amino acid groups. The shift in the pI's of the proteins and buffer's $pK_a$ follows directly from the Gibbs-Helmoltz equation:

$$\ln K_1 - \ln K_0 = \frac{\Delta H}{R}\left(\frac{1}{T_1} - \frac{1}{T_0}\right) \quad (1)$$

The ratio of the enthalpy of dissociation ($\Delta H$) to the gas constant, R, varies from approximately 600 for carboxylic acid groups to approximately 5500 for amino groups.

A temperature gradient or jump from, for example, 25° C. to 55° C. would produce a shift of about 0.2 pH units in the $pK_a$ of carboxylate groups but about 1.6 pH units for many amino groups. By shifting the pI's of the charged target molecules so as to widen the differences between them, the separation power of the method is increased. In many instances, the use of an isothermal shift will provide all of the flexibility needed to separate species with very similar pI's in a given temperature range.

Where temperature shift alone does not give a sufficiently robust separation, a temperature gradient approach may prove advantageous. The binding and separation properties of many ion exchange resins are relatively insensitive to a temperature change. This fact, combined with a known composition of an elution buffer, can be used to accurately predict the pH as a function of temperature. Since unrelated proteins or protein variants exhibiting nearly identical pIs at a given temperature almost always have a different set of ionizable residues, during elution through a temperature gradient their pIs will be changing at a different rate as a function of temperature causing them to move at a different rate. As a result, proteins that have strongly overlapping elution peaks in room temperature chromatofocusing (reverse chromatofocusing) will be well separated during the temperature gradient elution.

Comparison of Example 2 with Example 4 reveals that, for all of the proteins present in both examples, there is a relative shift of each protein's apparent (effective) pI towards a lower pH when the protein is separated on the anion exchanger as compared to its apparent pI on the cation exchanger. Conversely, there is a relative shift of apparent pI towards a higher pH when the protein is separated on the cation exchanger as compared to its apparent pI on the anion exchanger. For βLG, Conalbumin, Human Transferrin and Soybean Trypsin Inhibitor, for example, the pI shifts are well predicted by simple linear equations as follows:

apparent $pI$ on Mono $S$ cation exchanger=1.7019×[(apparent $pI$ on Mono $Q$ anion exchanger)−1.9034] or, alternatively apparent $pI$ on Mono $Q$ anion exchanger=0.5506×[(apparent $pI$ on Mono $S$ cation exchanger)+1.3516]

This behavior leads to a preferred aspect of the invention, providing for a combined external gradient chromatofocusing method of chromatographically separating charged molecules having different isoelectric points, comprising:

applying and binding the charged molecules to be separated to an anion exchange adsorbent perfused with a solvent comprising at least one buffering component at an initial maximum pH where the anion exchange adsorbent has a charge opposite that of the charged molecules;

supplying to the anion exchange adsorbent an eluent with a time dependent pH formed from the continuous mixing of a solution at the initial pH containing the at least one buffering component pumped out from a first reservoir with a solution at a different pH containing the at least one buffering component pumped out from a second reservoir, wherein the mixing proportions vary to maintain an unretained pH gradient with an externally defined slope;

eluting the charged molecules, each of which separately elutes from the anion exchange adsorbent at its effective isoelectric point, until a predetermined minimum pH is reached;

directing the resulting effluent from the anion exchange adsorbent containing the charged molecules into a cation exchange adsorbent to be further separated;

binding the charged molecules that are positively charged to the cation exchange adsorbent until the predetermined minimum pH is reached;

reversing the pH gradient perfusing the cation exchange adsorbent to develop from a predetermined minimum pH to a predetermined maximum pH; and collecting the charged molecules, each of which separately elutes from the cation exchange adsorbent at its effective isoelectric point, until the predetermined maximum pH is reached.

In this aspect, the cation exchange adsorbent is connected in series after the anion exchange adsorbent and equilibrated at the starting pH after the negatively charged molecules are bound to the anion exchanger and before the decreasing pH gradient is started. The anion exchange adsorbent is then disconnected from the cation exchange adsorbent after the positively charged molecules to be further separated are bound to the cation exchange adsorbent, and before the pH gradient is reversed to one that is increasing in time.

Another preferred aspect of the invention that is complementary to the anion-cation aspect described above provides for the separation of charged molecules having different isoelectric points, comprising:

applying and binding the charged molecules to be separated to a cation exchange adsorbent perfused with a solvent comprising at least one buffering component at an initial minimum pH where the cation exchange adsorbent has a charge opposite that of the charged molecules;

supplying to the cation exchange adsorbent an eluent with a time dependent pH formed from the continuous mixing of a solution at the initial pH containing the at least one buffering component pumped out from a first reservoir with a solution at a different pH containing the at least one buffering component pumped out from a second reservoir, wherein the mixing proportions vary to maintain an unretained pH gradient with an externally defined slope;

eluting the charged molecules, each of which separately elutes from the cation exchange adsorbent at its effective isoelectric point, until a predetermined maximum pH is reached;

directing the resulting effluent from the cation exchange adsorbent containing the charged molecules into an anion exchange adsorbent to be further separated;

binding the charged molecules that are negatively charged to the anion exchange adsorbent until the predetermined maximum pH is reached;

reversing the pH gradient perfusing the anion exchange adsorbent to develop from a predetermined maximum pH to a predetermined minimum pH; and collecting the charged molecules, each of which separately elutes from the anion exchange adsorbent at its effective isoelectric point, until the predetermined minimum pH is reached.

In this embodiment, the anion exchange adsorbent is connected in series after the cation exchange adsorbent and equilibrated at the starting pH after the positively charged molecules are bound to the cation exchange adsorbent and before the increasing pH gradient is started. The cation exchange adsorbent is disconnected from the anion exchange adsorbent after the negatively charged molecules to be further separated are bound to the anion exchange adsorbent, and before the pH gradient is reversed to one that is decreasing in time.

Yet another preferred aspect provides for a combined external gradient chromatofocusing method of chromatographically separating charged molecules having different isoelectric points, comprising:

applying the charged molecules to be separated to an anion exchange adsorbent, which is followed by a cation exchange adsorbent, (or, in a complementary aspect, a cation exchange adsorbent which is followed by an anion exchange adsorbent) perfused with a solvent comprising at least one buffering component at an initial pH where the charged molecules to be separated fall into at least one of the three charge classes: negatively charged, for those charged molecules that have apparent pIs below the initial pH; neutral for those charged molecules that fail to bind to either the anion exchange adsorbent or the cation exchange adsorbent at the initial pH; and positively charged for those charged molecules that have apparent p's above the initial pH;

binding the charged molecules which are negatively charged at the initial pH to the anion adsorbent;

binding the charged molecules which are positively charged at the initial pH to the cation adsorbent;

collecting those charged molecules which fail to bind to either adsorbent at the initial pH;

disconnecting the cation exchange adsorbent and the anion exchange adsorbent from each other at the initial pH;

supplying to the anion exchange adsorbent an eluent with a time dependent decreasing pH starting at the initial pH formed from the continuous mixing of a solution at the initial pH containing the at least one buffering component pumped out from a first reservoir with a solution at a different pH containing the at least one buffering component pumped out from a second reservoir, wherein the mixing proportions vary to maintain an unretained pH gradient with an externally defined slope; and collecting the charged molecules, each of which separately elutes from the anion exchange adsorbent at its effective isoelectric point, until a final minimum pH is reached;

supplying to the cation exchange adsorbent an eluent with a time dependent increasing pH starting at the initial pH formed from the continuous mixing of a solution at the initial pH containing the at least one buffering component pumped out from a first reservoir with a solution at a different pH containing the at least one buffering component pumped out from a second reservoir, wherein the mixing proportions vary to maintain an unretained pH gradient with an externally defined slope; and collecting the charged molecules, each of which separately elutes from the cation exchange adsorbent at its effective isoelectric point until a final maximum pH is reached.

The combined external gradient chromatofocusing methods provide additional flexibility in several ways. As a first illustration, the separation of STI and β-lactoglobulin on the anion exchange adsorbent, as shown in Example 2, is less than ideal. It can be seen that β-lactoglobulin is not well separated from the STI and appears as a shoulder on the left side of the STI peak. It is possible that the two proteins could be better separated by simply flattening the pH gradient. However, this will not always be the case. The failure to achieve an ideal separation in Example 2 can be used to illustrate a more general case wherein the apparent pIs of two or more components to be separated are too similar to allow an ideal separation. In contrast to the separation by EGCF (as shown in Example 2), the separation of the two proteins by EGRCF is excellent, as shown in Example 4. If the goal is to recover highly purified STI, then when the mixture of proteins shown in Example 2 is applied at pH 4.5 to a cation exchange adsorbent alone and elution is conducted with a pH gradient from pH 4.5 to pH 5.3, an excellent fractionation is achievable. In contrast, if STI is present in a very low concentration such that obtaining a sufficient quantity of purified protein requires applying a series of samples to the column, and if β-lactoglobulin and other proteins are unwanted pollutants present at a much higher concentration, then using EGRCF alone and applying the samples at a pH above 4.84, but below 5.72, causes each aliquot of STI to pass through the cation exchange adsorbent without binding, leaving almost all of the other constituents, including β-lactoglobulin, bound. As a result, fractions containing STI collected from a series of sample applications will be highly purified but significantly diluted, which is a major drawback because STI is already present at a very low concentration. If a series of samples is applied at a pH below 4.84, all of the STI will bind additively along with all of the unwanted proteins. Repeated sample applications would run the risk of saturating the cation exchange adsorbent. Using the EGRCF technique, the STI will now elute at a much higher concentration but the fraction containing it is likely to also include unwanted protein species because repeated application of unfractionated samples results in excessive amounts of protein bound to the column, or else some of the STI will be lost due to column saturation.

In the aspect of combined EGCF wherein the cation exchange adsorbent is followed by an anion exchange adsorbent connected in series, both of these limitations are addressed simultaneously. Application of the samples at a pH slightly above 4.84, such as, for example, 4.95, allows all of the STI to pass through the cation exchange adsorbent without binding, while virtually all of the unwanted proteins bind to the cation exchange adsorbent, including β-lactoglobulin. A pH of 4.95, which is well above the anion pI of STI at 4.09, results in STI binding to the anion exchange adsorbent. Finally, after completing the application of the samples to the cation exchange adsorbent, the cation exchange adsorbent is removed and the anion exchange adsorbent is eluted by either a pH step elution at pH 4.09 or a very narrow, negatively sloped pH gradient (such as from pH 4.2 to pH 3.9), yielding highly purified STI. Since the final elution occurs only from the anion exchange adsorbent, focusing efficacy is maximized and inadvertent contamination by background proteins is minimized.

If a more complex situation is considered, the advantages of combined EGCF become even clearer. Once again, proteins separated in Examples 2 and 4 will be used as an illustration. Consider a sample containing STI, β-lactoglobulin and HT in which both the STI and β-lactoglobulin are target proteins. Further, β-lactoglobulin is present at a very low concentration and HT is present in great excess. When using a single column, one would be constained to utilize EGRCF as in the previous example with the previously described limitations. With the combined chromatofocusing method, multiple samples would first be loaded on an anion exchange adsorbent alone at a pH just above 4.23. This action would result in all of the HT, but not STI and β-lactoglobulin, passing through the column without binding, thus eliminating HT as a potential contaminant. As a next step, a cation exchange adsorbent is attached below the anion exchange adsorbent and the tandem of columns is step washed with a solution having a pH below 4.09. At this pH, both the STI and β-lactoglobulin will elute from the anion exchange adsorbent, but will bind immediately to the second, cation, exchange adsorbent. In the final step, after removing the anion exchange adsorbent, a pH gradient is developed from pH 4.2 to pH 6, resulting in the elution of two cleanly separated fractions of STI and β-lactoglobulin. In a similar manner, any of the proteins shown in Examples 2 and 4 could be fractionated on a second column and eluted at very high purity. A demonstration of an embodiment of the combined EGCF technique is shown in Example 7.

In a preferred aspect of the combined chromatofocusing technique, a pH gradient separation is utilized on both the anion and cation adsorbents, which showcases the flexibility of this technique. Once again, reference is made to Examples 2 and 4. Consider a sample in which STI, HT and Conalbumin are target products but HT is present in very low abundance.

It is required that the concentration of the HT be greatly increased. Initially, the protein mixture is applied and bound to the anion adsorbent at a pH of 6.8. Following the proteins' binding, a cation adsorbent is attached in series after the anion adsorbent and both exchangers are equilibrated at pH 6.8. Next, a descending pH gradient is developed from pH 6.8 to pH 4.8. When the pH gradient starts to elute Conalbumin at pH 6, the effluent is directed away from the cation adsorbent and the protein is collected as a first purified product. After collection of the Conalbumin, the effluent is redirected back into the cation adsorbent. In the pH range 5.3 to 4.8, HT is eluted from the anion adsorbent but binds to the cation adsorbent because it is positively charged and its apparent cation pI is 6.37. As the pH gradient progresses and the pH falls below 4.8, the effluent is again directed away from the cation adsorbent and, in the pH range 4.3 to 4.0, a fraction of STI is eluted from the anion adsorbent as a second purified product. After the collection of STI is completed, the anion adsorbent is disconnected from the cation adsorbent, cleaned and re-equilibrated at pH 6.8, another protein sample to be separated is loaded, and the same procedure of fractionation is repeated. It is not necessary to re-equilibrate the cation adsorbent at the initial pH of 6.8 because the pH gradient effluent from the next fractionation will enter the cation exchanger again starting at pH 5.3. This pH is well below the apparent cation pI of HT and therefore will not dislodge HT previously bound to the cation adsorbent. When a sufficient accumulation of HT on the cation adsorbent is achieved, the protein is either eluted by a reverse pH gradient from pH 6 to pH 6.6 or a step pH eluted at pH 6.37. Using the described protocol of combined chromatofocusing allows all three proteins to be well separated, and one of them in a highly concentrated state.

In another aspect of the combined EGCF technique, the temperature of either column individually, or both columns simultaneously, can be varied over the working temperature range of the adsorbent(s) and the buffer solutions. Use of temperature as a means of enhancing separation may be necessary when the pI shift of a particular target molecule during separation at room temperature is small in going from a cation to an anion binding environment or conversely, from an anion to a cation binding environment.

While proteins are the preferred charged molecules for separation by the methods of the invention, other suitable charged molecules include, but are not limited to, RNA, polyampholytes, aminosugars, charge-bearing polysaccharides containing uronic acids and charged aromatic compounds such as tannins (protein-binding polyphenolic acids) naturally occurring in plants.

Appropriate solvents for use in the chromatographic systems of the invention include, but are not limited to, water and suitable organic solvents that are known in the art. Water is the preferred solvent.

The buffering components utilized in the chromatographic systems of the invention have overlapping pKa's. During chromatographic separation of mixtures of charged molecules, the molar proportion of each buffer component may either remain constant or change throughout the transition between the initial pH and the final pH. Each buffering component of the buffering compositions of the invention contains at least one functionality selected from the group consisting of amino, amido, imino, imido, carboxylic, sulfonic, phosphoric and phosphonic and is present in a concentration of about 0.001 mM to about 1000 mM. Examples of suitable buffer components include, but are not limited to, 1,2,3-triaminopropane, 1,2-di-(2-aminoethylthio)ethane, 1,2-diamino-2-methylpropane, 1,2-diaminopropane, 1,3-diamino-2,2-dimethylpropane, 1,3-diaminopropan-2-ol, 1,3-diaminopropane, 2-(2-hydroxypropylamino) ethylamine, 2-(3-hydroxypropylamino), ethylamine, 2,2'-diaminodiethyl sulfide, 2,2'-diaminodiethylamine, 2,2'-dihydroxydiethylamine, 2,3-diamino-2,3-dimethylbutane, 2,3-diaminobutane, 2-amino-2'-hydroxydiethyl sulfide, 2-aminoethylsulphonic acid, 2-carboxyethyliminodiacetic acid, 2-methoxyethylamine, 2-methoxyethyliminodiacetic acid, 2-methyl-4-hydroxy-aminobenzimidazole, 2-methylbenzimidazole, 2-methylimidazole, 2-methylthioethylamine, 2-methylthioethyliminodiacetic acid, 2-phosphonoethyliminodiacetic acid, 2-thienylmethylamine (2-thiophenemethanamine), 3,3'-diaminodi-n-propylamine, 3-hydroxypropyliminodiacetic acid, 4-(2-aminoethyl)morpholine, 4-bromoimidazole, 4-hydroxy-6-aminobenzimidazole, 4-hydroxybenzimidazole, 4-hydroxymethylimidazole, 4-methoxybenzimidazole, 4-nitroimidazole, 6-nitrobenzimidazole, ACES (N-(carbamoylmethyl)-2-aminoethanesulfonic acid), acetic acid, ADA (N-(2-acetamido)-2-iminodiacetic acid), adipic acid, AlaAlaAla (alanylalanylalanine), alanine, aminomalonic acid (aminopropanedioic acid), AMP (2-amino-2-methyl-1-propanol), AMPD (2-Amino-2-methyl-1,3-propanediol), AMPSO (3-[(1,1-Dimethyl-hydroxyethyl)amino]-2-hydroxypropanesulfonic acid), arginine, aspartic acid, aspartylhistidine, azelaic acid (1,7-heptanedicarboxylic acid), benzoic acid, benzylglutamic acid, BES (N,N-bis(2-hydroxyethyl)-2-aminoethanesulfonic acid), BICINE (N,N-bis(2-hydroxyethyl)glycine), BIS-TRIS (2-bis(2-Hydroxyethyl)amino-2-(hydroxymethyl)-1,3-propanediol), BIS-TRIS PROPANE (1,3-bis[tris(hydroxymethyl)methylamino]propane), butanoic acid, CABS (4-(cyclohexylamino)-1-butanesulfonic acid), CAPS (3-(cyclohexylamino)-1-propanesulfonic acid), CAPSO (3-(cyclohexylamino)-2-hydroxy-1-propanesulfonic acid), CHES (2-(cyclohexylamino)ethanesulfonic acid), citric acid (2-hydroxy-1,2,3-propanetricarboxylic acid), cysteine, cystine, cystinyldiglycine, di-(2-hydroxyethyl)aminoacetic acid, di-(carboxymethyl)-aminomethyl phosphonic acid, diethanolamine, diethylaminoacetic acid, diethylmalonic acid, diglycylcystine, dimethylaminoacetic acid, dimethylmalonic acid, di-n-propylmalonic acid, DIPSO (N,N-bis(2-hydroxyethyl)-3-amino-2-hydroxypropane sulfonic acid), DL-1:2-dichlorosuccinic acid, DL-1:2-dimethylsuccinic acid, D-tartaric acid, EDTA (ethylenediamine tetraacetic acid), EPPS (N-(2-hydroxyethyl)piperazine-N'-(3-propanesulfonic acid)), ethanolamine, ethylenediamine, ethylenediamine-N,N'-diacetic acid, ethylenediamine-N,N-diacetic acid, ethylmalonic acid, ethyl-n-propylmalonic acid, formic acid, fumaric acid, glutamic acid, glutaric acid, glutathione-γ-L-glutamyl-L-cysteinylglycine, GlyAla (glycylalanine), GlyAlaAla (glycylalanylalanine), glycine, glycine amide (2-aminoacetamide), glycolic acid, GlyGly (glycylglycine), GlyGlyGly (glycylglycylglycine), GlyPro (glycylproline), HEPBS (N-(2-hydroxyethyl)piperazine-N'-(4-butanesulfonic acid)), HEPES (N-(2-hydroxyethyl)piperazine-N'-(2-ethanesulfonic acid)), HEPPSO(N-(2-hydroxyethyl)piperazine-N'-(2-hydroxypropanesulfonic acid)), hexamethylenetetramine, histidine, histamine (1H-imidazole-4-ethanamine), histidyltyrosine, homocystine (4,4'-Dithiobis(2-aminobutanoic acid)), hydroxyquinoline, imidazole, iminodiacetic acid, iminodipropionic acid, i-propylmalonic acid, lactic acid, leucine, lysine, maleic acid, malonic acid, mercaptoethylamine, MES (2-(N-morpholino) ethanesulfonic acid), meso-1:2-dibromosuccinic acid, meso-1:2-dichlorosuccinic acid, meso-1:2-dimethylsuccinic acid, meso-tartaric acid, methyl-[β-diethylamino-ethyl]sulfide, methylethylmalonic acid, methyliminodiacetic acid, methylmalonic acid, methyl-α-amino-β-mercaptopropionate, MOBS (4-(N-morpholino)butanesulfonic acid), MOPS (3-(N-Morpholino)propanesulfonic acid), MOPSO (2-hydroxy-3-morpholinopropanesulfonic acid), N-(2-hydroxyethyl)-ethylenediamine, N-(carbamoylmethyl)-iminodiacetic acid, N,N'-di-(2-aminoethyl) ethylenediamine, N,N'-diethylethylenediamine, N,N-diethylethylenediamine, N,N'-diglycylethylenediamine, N,N'-dimethylethylenediamine, N,N-dimethylethylenediamine, N,N-dimethylhydroxylamine, N,N'-di-n-propylethylenediamine, N-2-hydroxyethyliminodiacetic acid, N-2-sulfoethyliminodiacetic acid, N-acetylhistidine, N-allylmorpholine, N-allylpiperidine, N-butylaminoacetic acid, N-diethyl-cysteamine, N-dimethyl-cysteamine, N-dipropyl-cysteamine, N-ethylaminoacetic acid, N-ethyl-ethylenediamine, N-ethylmorpholine, N-ethylpiperidine, N-isopropylaminoacetic acid, N-isopropylethylenediamine, nitrilotriacetic acid, N-methylaminoacetic acid, N-methyldiethanolamine, N-methylethylenediamine, N-methylmorpholine, N-methylpiperazine (1-methylpiperazine), N-methylpiperidine, N-methylpyrrolidine, N-methyltrimethyleneimine, N-n-butylethylenediamine, N-n-propylaminoacetic acid, N-n-propylethylenediamine, n-propylmalonic acid, N-β-mercaptoethyl-morpholine, N-β-mercaptoethyl-piperidine, O,O'-diethylsuccinic acid, O—O'-dimethylsuccinic acid, oxalic acid, phthalic acid, pimelic acid, piperazine, piperidine, PIPES (piperazine-N,N-bis(2-ethanesulfonic acid)), PIPPS (piperazine-N,N'-bis(3-propanesulfonic acid), POPSO (piperazine-N,N-bis(2-hydroxypropanesulfonic acid)), proline, salicylic acid, sarcosine (N-methylglycine), suberic acid, serine, succinic acid, sulfanilic acid, TABS (N-tris-(hydroxymethyl)methyl-4-aminobutanesulfonic acid), TAPS ([(2-hydroxy-1,1-bis[bydroxymethyl]ethyl)amino]-1-propanesulfonic acid), TAPSO (3-(N-tris[hydroxymethyl]methylamino)-2-hydroxypropanesulfonic acid), taurine (2-aminoethanesulfonic acid), TES (2-[(2-hydroxy-1,1-bis[hydroxymethyl]ethyl)amino]ethanesulfonic acid), tetramethyl succinic acid, triaminotriethylamine, threonine, TRICINE N-[tris(hydroxymethyl)methyl]-glycine, triethanolamine, triethylenediamine, tricarballylic acid (1,2,3-propanetricarboxylic acid), tryptophan, tyrosine, TRIS (tris(hydroxymethyl)aminomethane); α,α-diaminobutyric acid; α,β-diaminopropionic acid; α,β-dimercaptosuccinic acid; β-ethylglutaric acid; β-n-propylglutaric acid; β,β-diethylglutaric acid; β,β-dimethylglutaric acid; β,β-di-n-propylglutaric; β,β-methylethylglutaric acid, β-carboxymethylaminopropionic acid β-methylglutaric acid and valine.

In a preferred aspect, the buffering components comprise piperazine, 1-methyl piperazine, triethanolamine, bis-tris propane and optionally, formic acid.

The buffering compositions containing the buffering components have the property that when the composition at a predetermined pH is titrated with the buffer composition at a different predetermined pH, the change in the pH of the mixture of the two compositions will be directly linearly proportional to the fraction of the mixture represented by each of the two compositions. Typically, the difference between the predetermined pH and the different predetermined pH is anywhere from 1 pH unit to 10 pH units. The pH is generally measured at the exit of the ion exchange column.

Suitable adsorbents for use in the methods of the invention are weak anion exchange resins, weak cation exchange resins, strong anion exchange resins and strong cation exchange resins. Exemplary resins include, but are not limited to quaternary ammonium strong anion exchangers such as Mono Q (Amersham Pharmacia), 300VHP (Vydac), SynChropak SAX (Agilent Technologies) and COSMOGEL QA (Nacalai Tesque, Inc.); methyl sulfonate strong cation exchangers such as Mono S (Amersham Pharmacia); sulfopropyl strong cation exchangers such as SP Sepharose (Amersham Pharmacia), 400VHP (Vydac), TSK SP-5PW (Agilent Technologies) and COSMOGEL SP (Nacalai Tesque, Inc.); mixed quaternary and tertiary amines weak anion exchangers such as Mono P (Amersham Pharmacia); diethylaminoethyl DEAE weak anion exchangers such as DEAE Sepharose (Amersham Pharmacia), Protein Pack DEAE 5PW (Waters), TSK DEAE-5PW (Agilent Technologies) and 301VHP tertiary amine (moderate-DEAE type) anion exchanger (Vydac); diethylaminopropyl weak anion exchangers such as ANX Sepharose 4FF (Amersham Pharmacia); carboxymethyl weak cation exchangers such as CM Sepharose FF (Amersham Pharmacia), SynChropak WCX (Agilent Technologies), IEC CM-825 (Shodex), STYROS™ CM (OraChrom, Inc.) and COSMOGEL CM (Nacalai Tesque, Inc.); polyethyleneimine ion exchanger columns such as PL 1000 SAX, SynChropak WAX (Agilent Technologies) and weak anion exchanger crosslinked polyethyleneimine phases MICRA-Gold AX100, AX1000 and MICRA-Silver AX300 (Eichrom Technologies, Inc.).

The difference between the initial pH and the final pH employed in a typical chromatographic separation varies greatly and is dependent on factors such as the buffering species included in the buffer solutions allowing the formation of a stable linear external pH gradient over the pH range of interest, the pI's of the compounds to be separated, the closeness of the pI's of the compounds to be separated and the width of the pH range over which the experimenter can control the shape of the gradient. Generally, the difference can be anywhere from about 1 pH unit to about 12 pH units. When the adsorbent is an anion exchange adsorbent, the initial pH is higher (i.e. more alkaline) than the final pH while when the adsorbent is a cation exchange adsorbent, the initial pH is lower (i.e. more acidic) than the final pH.

In one of the aspects of the invention that provide for heterothermal ExGC and heterothermal RevExGC, the adsorbent can be heated such that there is an increasing temperature gradient along the adsorbent from where the charged molecules are added to where the separated charged molecules are collected. In another aspect, the adsorbent can be cooled such that there is a decreasing temperature gradient along the adsorbent from where the charged molecules are added to where the separated charged molecules are collected. In both embodiments, the range of the temperature gradient is between 0° C. and 80° C.

Other aspects of the invention provide for a chromatographic system for low or high pressure liquid chromatography for separation of charged molecules by ExGC and RevExGC with a feedback system that allows automated, controlled formation of the elution external pH gradient. This chromatographic system contains the elements typically present in a liquid chromatograph such as, for example, a dual pump block, mixer, injection valve, light detector or other type of detector for monitoring molecule separation, pressure transducers, fraction collector and computer. Amersham Biosciences offers liquid chromatographic systems such as ÄKTAexplorer, ÄKTApurifier, ÄKTAFPLC (FPLC—fast protein liquid chromatography) and ÄKTApilot which have advanced combined detectors monitoring simultaneously, absorbance, conductivity and pH (by a pH flow cell) and which currently can be used in the separation of charged molecules by retained gradient chromatofocusing. With the addition of a feedback pH controlling system as described in this invention, commercial low pressure liquid chromatography or HPLC systems can be easily adapted to automatically control pH gradient formation for ExGC (or RevExGC) of charged molecules.

In aspects of chromatographic systems for ExGC (or RevExGC), either a relatively small pH flow cell (as exemplified in FIG. 6 Panel A) or a pH electrode immersed in a mixing chamber (as exemplified in FIG. 6 Panel B) is used as pH measuring and feedback signal generating devices. As discussed above, in ExGC (or RevExGC) the formation of a pH gradient is virtually independent of the properties of the strong ion exchange resin packed in the column. That is why the pH feedback device is typically situated upstream from the separation column. The embodiments of this chromatographic system with a small pH flow cell feedback system (as exemplified in FIG. 6 Panel A) are preferably, but not limited to use with pH gradient forming solutions containing more than one buffering component such that no large pH changes can occur as a result of minor changes in the proportions of solutions being pumped from pumps A and B.

In a preferred aspect, the pH controlling-correcting process for the chromatographic system with a mixing chamber (as exemplified in FIG. 6 Panel B) is described as follows. The column is initially equilibrated with pH solution A that fills the mixing chamber. Further, pumps A and B are set to an initial rate causing the pH in the eluent stream to begin to change in the direction of the final pH because of the addition of pH solution B into the mixing chamber. Pump C is set to pump at either a constant or varying pumping rate. The pH electrode continuously measures an actual change in pH as a change in voltage which is delivered to the feedback controlling unit, which is effectively a computer with a feedback-control electronic board or a feedback controller that is programmable or computer controlled. The feedback controlling unit has an algorithm or lookup table for determining the voltage expected if the pH were to change exactly according to the preprogrammed gradient. This is termed the ideal voltage. The unit then calculates the difference between the actual voltage and the ideal voltage ($-\Delta V$). This difference is then transformed with one of several available feedback control algorithms such as DET (Dynamic Equivalence-point Titration)—used in automatic titrators such as Mettler Toledo DL58 with LabX titration software—Brochure, Automatic and flexible DL5x and DL7x titration systems, 2003; Metrohm Titrino 716—Metrohm Ltd. 716 DMS Titrino, Metrohm AG, Herisau, Switzerland, 1992); PID (Proportional Integral Derivative)—for example, the YS170 pH Controller produced by Yokogawa Corporation of America, Application Notes); Neural Network (W. L. M. N. Karim, A. J. Morris, and E. B. Martin, Comput. Chem. Eng., 20:S1017-S1022, 1996), Neural Network Applications in Control, Edited by G. W. Iwin, K. Warwick and K. J. Hunt 1995); Fuzzy Logic (S. Menzl, M. Stühier, and R. Benz, Wat. Res., 30(4):981-991, 1996); R. Babuska, J. Oosterhoff, A. Oudshoom, P. M. Bruijn, Engineering Applications of Artificial Intelligence 15 (1) (2002) pp. 3-15) etc. so as to generate a correction voltage to be sent to pumps A and B to accelerate or decelerate them such that the absolute value of the next measured $\Delta V$ is as small as possible and to maintain the $\Delta pH$ in the preprogrammed range. Pump C can be set to pump at a constant rate such that the volumes of the solution in the mixing chamber at the beginning and at the end of the pH gradient formation are equal. Alternatively, the pumping rate could be any pumping rate such that the net change in solution volume in the mixing chamber will not compromise control of the pH gradient formation. As long as the stepwise corrections to the individual pumping rates of pumps A and B are small compared to the total pumping rate, control of the external pH gradient can be maintained by the feedback systems. This can be illustrated by a challenging example of RevExGC, with a pH gradient formation over a wide pH range using only one weak acid (acetic acid) and only one strong base, potassium hydroxide (KOH), in reservoir B. Initially pump A is used to fill and maintain a constant volume of the solution in the mixing chamber while pump C pumps out acetic acid to perfuse and equilibrate a strong cation exchange column. At the beginning of pH gradient formation, pump A is switched off. The performance of the feedback system will be examined at the starting pH, at the pH of maximum buffering capacity ($pK_a$) where the pumping rate from B will be maximal, at a pH as far above $pK_a$ as the starting pH is below it, and at the final pH where there will be almost no buffering capacity and the pumping rate will be minimal. The concentration of acetic acid is 10 mM and thus the starting pH will be very close to 3. Reservoir B contains 300 mM KOH at pH 13. The experimenter decides to ramp the pH at a constant $\Delta ph$ of 0.1 pH unit/min from pH 3 to pH 9 at a constant elution rate of 1 ml/min. The mixing chamber is set up with a maximum capacity of 3.5 liters and is filled with 3 liters of 10 mM acetic acid. At pH 3 the acetic acid is 98.2% associated whereas at pH 3.1 it will be 97.8% associated (i.e. a 40 μM reduction of the concentration of the associated acid). Thus, because there are 3 liters of solution, in order to change the pH by 0.1 unit, 120 μmoles of KOH has to be added in the first minute. Each ml of KOH contains 300 μmoles of KOH so one must begin adding the KOH at 0.4 m/min. The maximum buffering capacity of the acetic acid occurs at $pH=pK_a=4.75$ where it is 50% dissociated. At pH 4.75 there are 15 mmoles of undissociated acid in the chamber. At pH 4.85 there will be 13.27 mmoles of undissociated acid (i.e. 1.73 mmoles of KOH need to be added to induce the 0.1 pH unit change). Thus the maximum pumping rate for pump B will approach 5.77 ml/min, which is well within the capability of available pumps. By the time the system has reached pH 6.5, the amount of KOH needed to titrate to pH 6.6 would be approximately 100 μmoles for a pumping rate in the 0.3-0.4 ml/min range. Finally, if one assumes that the pH has reached 8.9 in control, the addition of base to achieve pH 9.0 in one minute must now be very small because very little associated acetic acid remains. The system limitation will now be that the calculated pumping rate (i.e. the addition of KOH) of pump B does not fall below the lowest pumping rate of which the pumps are capable. At pH 8.9 there will be 2.1 μmoles of associated acid left in the mixing chamber to be dissociated. At pH 9.0 there will be 1.7 μmoles of associated acid remaining. Thus 0.4 μmoles of KOH per min has to be delivered to induce the 0.1 pH unit/min increase (i.e. the pumping rate will have to be 1.3 μl/min). Available laboratory pumps (e.g. the Jasco HPLC series) have an effective range of pumping rates from 1 μl/min to 10 ml/min. It should be noted that, because KOH has been added continuously with pump A nonoperational, the acetic acid concentration has fallen. To a good first approximation, the acetic acid concentration decrease is calculated by the dilution of the initial acetic acid into the total volume. The time of pH gradient formation is 60 minutes, so 60 ml is removed in that time by pump C. The mean pumping rate for the KOH is approximately 3 ml/min for the first 40 minutes, but no more than about 0.2 ml/min for the last 20 min. This computes to a net total volume of about 3,064 ml in the mixing chamber at the end of the pH gradient formation. Thus, there will be no more than about a 2% reduction in the concentration of acetic acid. Because of the addition of the concentrated KOH, the concurrent change in molarity of the solution would be from 10 mM to about 22 mM, well within an acceptably low level of ionic strength.

This example was used particularly to illustrate that an extremely simple and inexpensive buffering chemistry could achieve very powerful results. In fact, the relative simplicity of calculating the change in pH in the mixing chamber as a function of adding strong base or acid to a single weak acid or base throughout the range of a pH gradient allows a computer program with a simple calculational algorithm to drive the pumps with the feedback control system providing backup correction. However, the more complex the buffering chemistry, the more cumbersome the calculational algorithms become and it is anticipated that in most preferred aspects two or more weak acids or bases will initially be present in the mixing chamber. Use of solutions with multiple buffering compounds in combination with a feedback control system allows pumping at modest rates throughout the required pH range while maintaining an accurate pH gradient without the need for new, complex algorithmic changes corresponding to every change in the chemistry of the titrating solutions.

EXAMPLES

All chromatographic separations presented in the examples were carried out on a computer controlled ACT-A$_{FPLC}$ fast protein liquid chromatography system (Amersham Pharmacia Biotech, Uppsala Sweden) equipped with, P-920 pumping system, Mixer M-925, UPC 900 monitor, Hg optics, 5 mm flow cell, conductivity cell and Fraction collector Frac-900. The elution of the proteins from the column was monitored following the effluent UV absorbance at 280 nm or 254 nm. Fractions of 1 or 0.5 ml were collected during each separation and their pH measured immediately after completion of the experiment on a PHM 82 standard pH meter (Radiometer, Copenhagen Denmark). The columns Mono Q HR 5/5 strong anionic exchanger, Mono S HR 5/5 strong cationic exchanger and Mono P HR 5/20 weak anionic exchanger were purchased from Amersham Pharmacia Biotech. Triethanolamine was from Sigma (St. Louis, Mo. USA), iminodiacetic acid, piperazine, methyl-piperazine and formic acid were from Aldrich (Milwaukee, Wis. USA), Bis-Tris Propane from ICN Biomedicals Inc. (Irvine, CA USA) and Polybuffer 96, Polybuffer 74 were from Amersham Pharmacia Biotech. Proteins were obtained from Sigma (St. Louis, Mo. USA) and Calbiochem (San Diego, Calif. USA) and used without further purification. The pH gradient forming solutions were freshly prepared before each experiment by dissolving the buffering species in water at the necessary concentration, titrated to their respective pH with hydrochloric acid, diluted to the final volume and vacuum filtered through a 0.45 μm filter. Unless otherwise indicated the following procedure was used to perform all separations. One to two mg of the proteins to be separated were dissolved in the starting pH buffer and filtered through a 0.45 μm low protein binding filter. Before each separation the column was equilibrated with at least 10 column volumes of starting buffer (until the pH of the effluent equaled the pH of starting buffer). The protein sample was then applied to the entrance of the column and the column was washed with 3 to 5 column volumes of starting buffer (until no change in absorbance could be detected in the effluent) to remove the unbound material. Subsequently without stopping the pumps, a computer controlled external gradient chromatofocusing (reverse chromatofocusing) separation was performed by executing a pre-programmed chromatographic method through the software (Unicorn V.3) of the ACTA$_{FPLC}$ system. The method contained information about the elution flow rate, the length and the shape of the preformed external pH gradient to be applied to the column, properties of the column, and pre- and post-elution times.

Collection of data was ended upon completion of the gradient formation at the pH of the final buffer and washing of the column with 2-7 column volumes of final buffer. Although the presented examples demonstrate relatively small scale analytical separations the methods of external pH gradient chromatofocusing and reverse chromatofocusing developed on analytical columns, e.g. Mono Q and Mono S HR 5/5, are easily scaleable and can be used for large scale purifications on bigger columns e.g. Mono Q, Mono S HR 10/10, HR 16/10 or bigger.

Example 1

External gradient chromatofocusing separation of a complex mixture of proteins on a strong anion exchanger Mono Q HR 5/5 at room temperature. Starting buffer A-5 mM Methyl Piperazine, 5 mM Piperazine, 5 mM TE pH 9.5, final buffer B-5 mM Methyl Piperazine, 5 mM Piperazine, 5 mM TE pH 3.5. Flow rate 1 ml/min, length of linear gradient formation from 0% B to 100% B 40 column volumes. The three component buffer system used to form the external gradient in this example exhibits a pH profile with moderate non-linearity (FIG. 1, panel B, dotted line). Despite the complexity of the sample, the closeness in pI's for several species and the wide pH range necessary to separate all components an excellent resolution is achieved (FIG. 1, panels A and B).

Example 2

Figure 2:
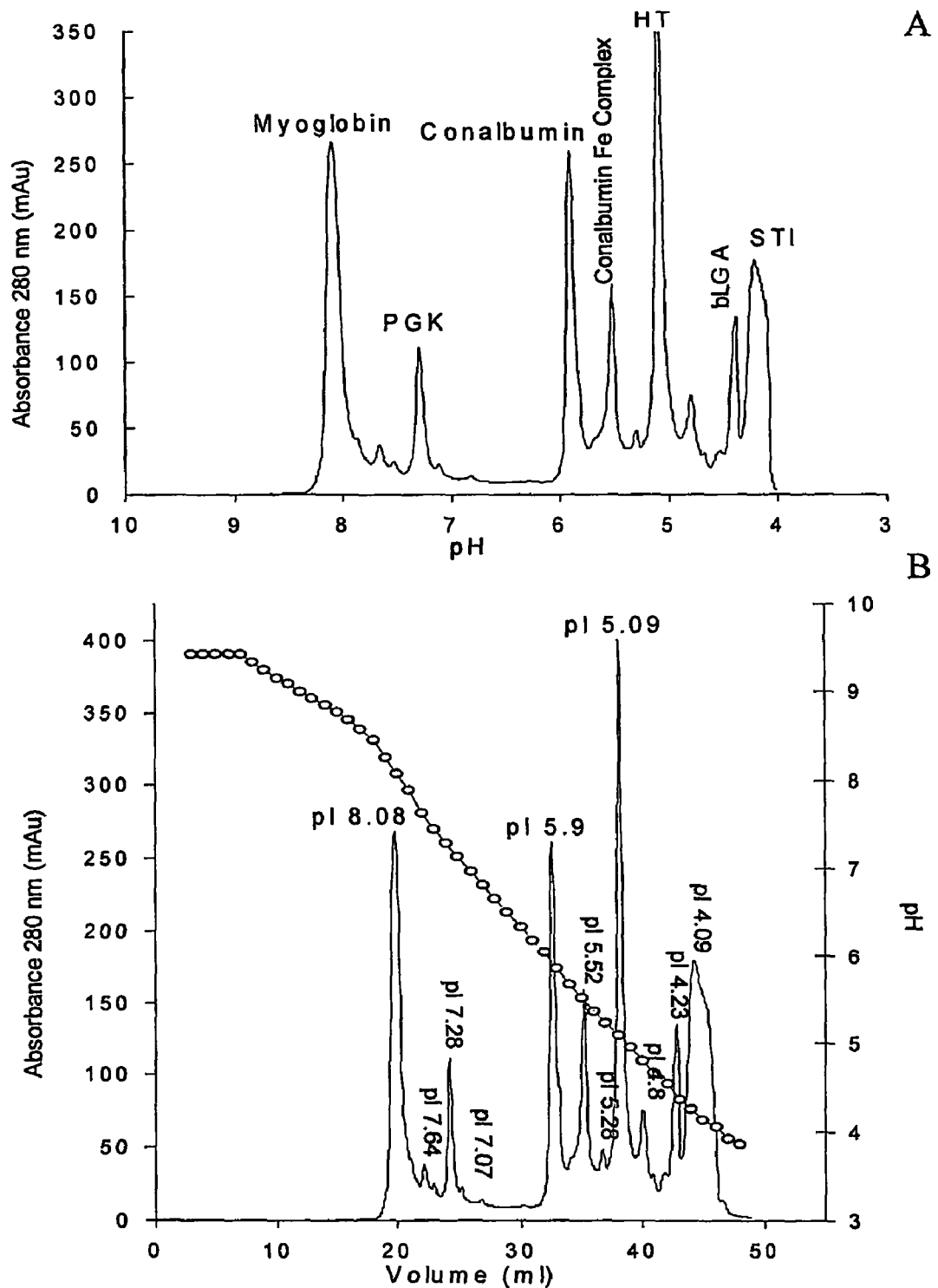
FIG. 2. This figure depicts the separation of a complex mixture of proteins by chromatofocusing on a strong anion exchange column using a four-component buffer system.

A protein mixture with the same composition as in Example 1 separated by external gradient chromatofocusing on a strong anion exchanger Mono Q HR 5/5 at room temperature using the invention's four component buffer system. Starting buffer A-4 mM Tris-Bis Propane, 4 mM Methyl Piperazine, 4 mM Piperazine, 4 mM TE pH 9.5, final buffer B-4 mM Tris-Bis Propane, 4 mM Methyl Piperazine, 4 mM Piperazine, 4 mM TE pH 3.5. Flow rate 1 ml/min, length of linear gradient formation from 0% B to 100% B 40 column volumes. The improvement in separation is not significant but the addition of Bis-Tris Propane to the gradient forming solutions (A and B) makes the pH profile much more linear (FIG. 2, panel B. dotted line). FIG. 2, panel A shows the UV absorbance of the separated protein species vs. pH.

Example 3

Figure 3:
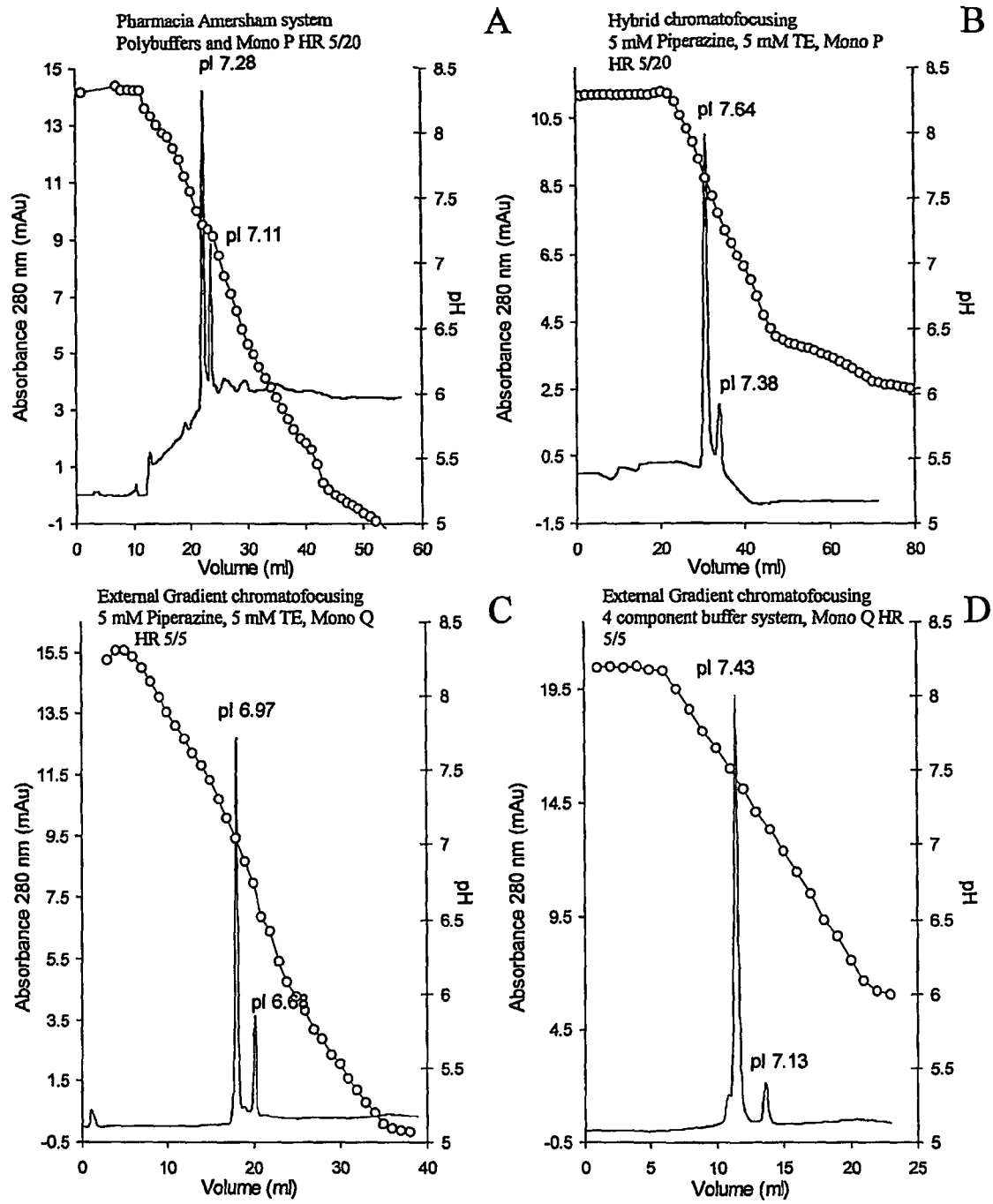
FIG. 3. This figure depicts a comparison of the separation of two variants of yeast phosphoglycerate kinase employing various chromatofocusing techniques.
Figure 4:
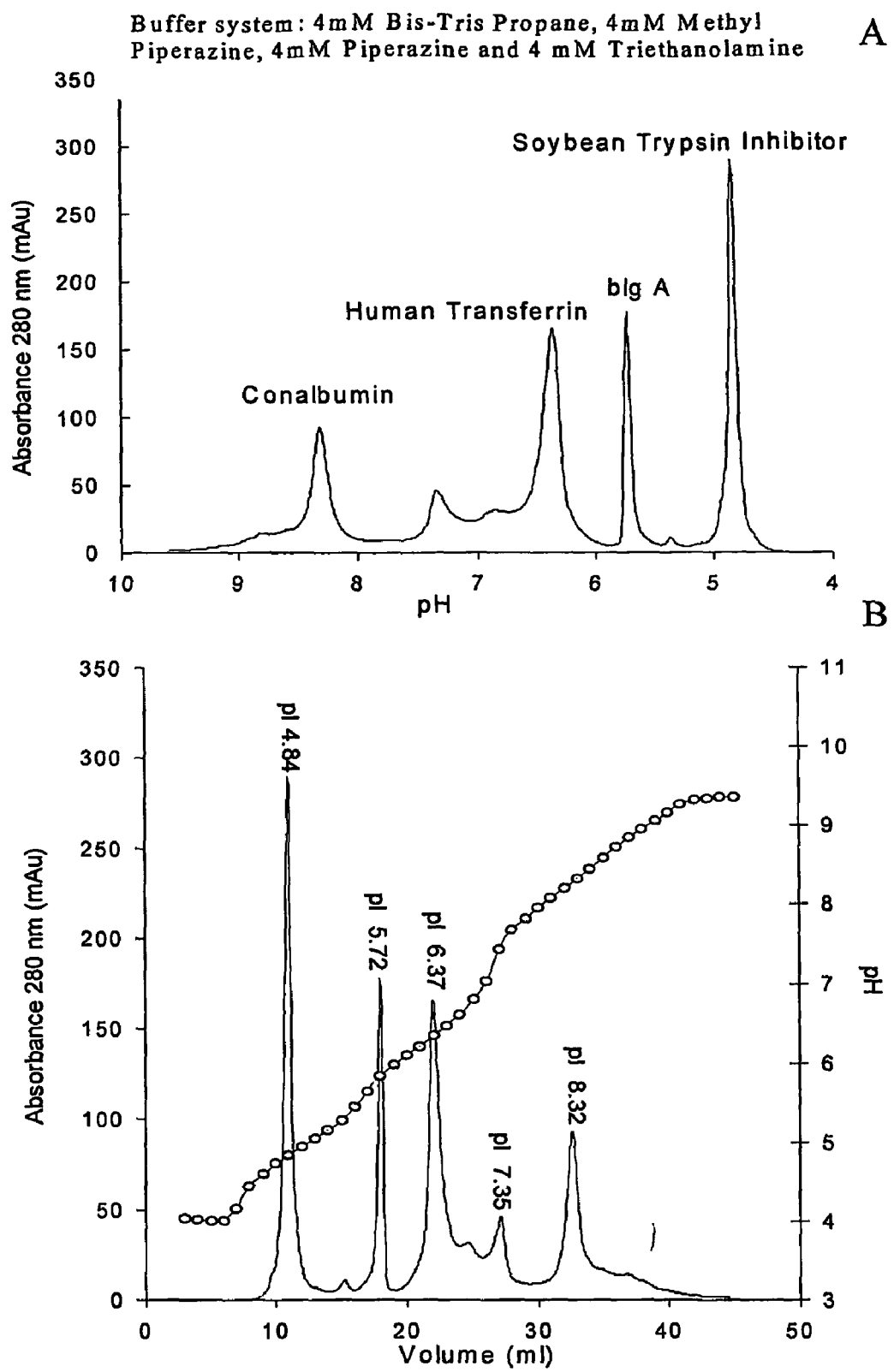
FIG. 4. This figure depicts the separation of a mixture of proteins by external gradient reverse chromatofocusing on a strong cationic exchange column using a four-component buffer system.
Figure 5:
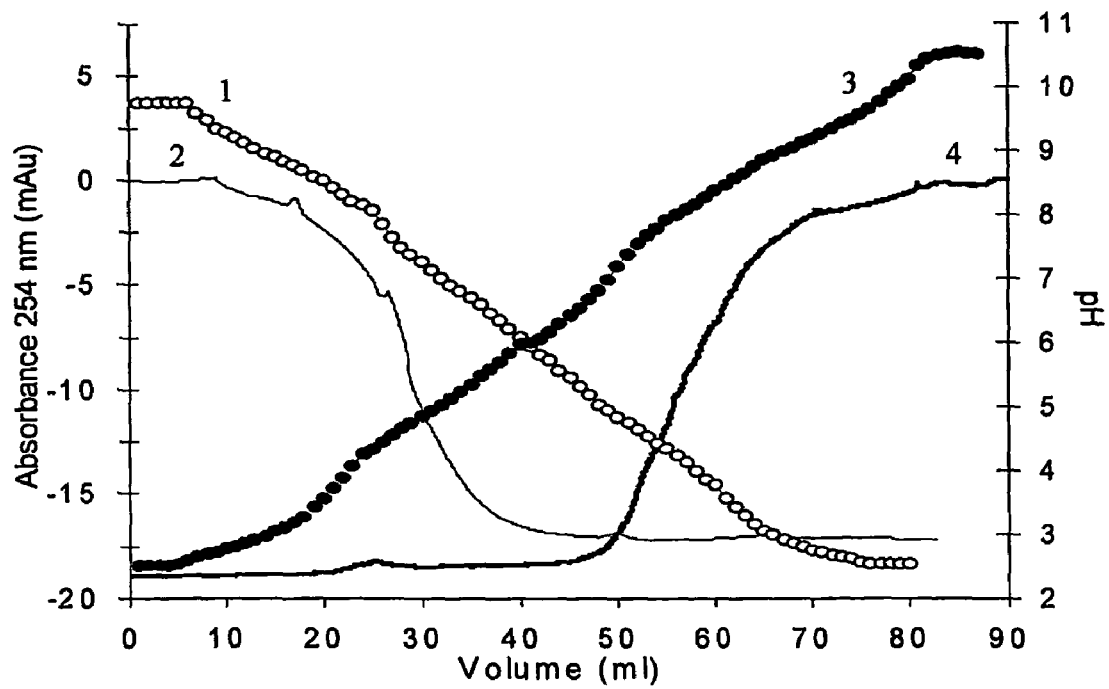
FIG. 5. This figure shows the pH, absorbance and conductivity of the effluent as well as the traces of the preprogrammed external gradient demonstrating the applicability of a wide pH range buffering system (Starting buffer: 4 mM Bis-Tris Propane, 4 mM Methyl Piperazine, 4 mM Piperazine and 4 mM Triethanolamine pH 9.7 for Mono Q HR 5/5 or pH 10.5 for Mono S HR 5/5. Final buffer: 4 mM Bis-Tris Propane, 4 mM Methyl Piperazine, 4 mM Piperazine, 4 mM Triethanolamine and 2 mM Formic acid pH 2.5) in chromatofocusing and reverse chromatofocusing techniques. Flow rate 1 ml/min, length of external gradient formation (elution) upon chromatofocusing 73 column volumes and during reverse chromatofocusing 81 column volumes.
Figure 5:
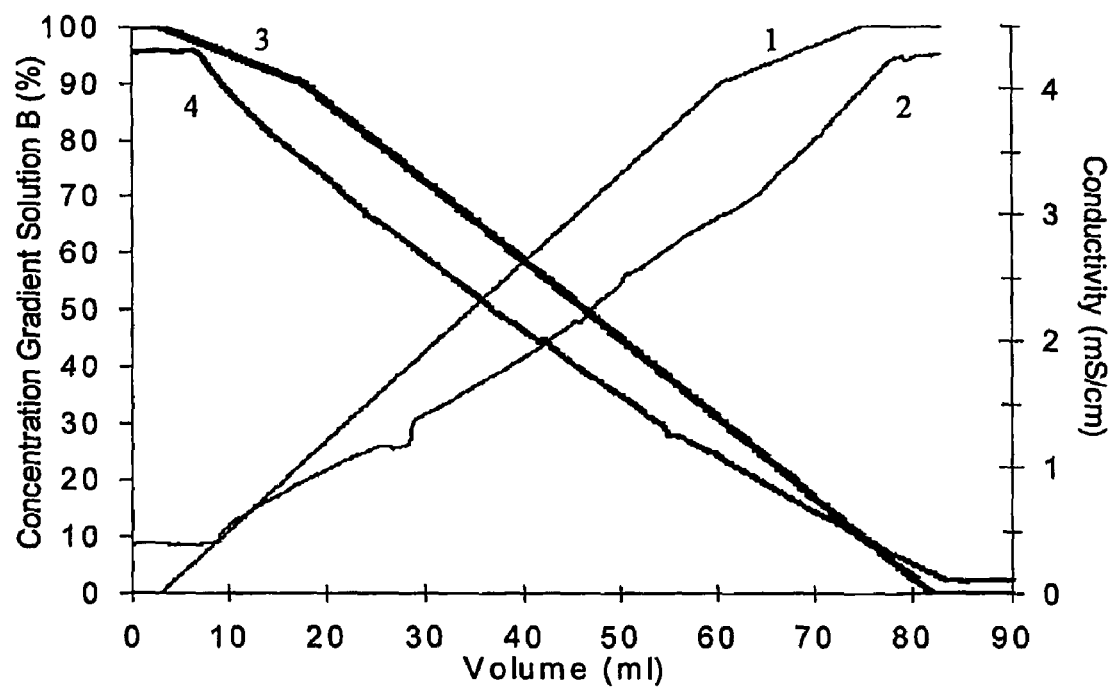

Comparison of separations of two variants of yeast phosphoglycerate kinase 0.2 mg by internal retained pH gradient chromatofocusing and external pH gradient chromatofocusing on weak and strong anionic exchanger. Panel A Chromatofocusing with Polybuffers and Mono P HR 5/20 column offered by Pharmacia Amersham Biotech Equilibration buffer A-25 mM TE iminodiacetic acid pH 8.3 elution buffer B-6 ml Polybuffer 96+14 ml Polybuffer 74, iminodiacetic acid pH 5 diluted to 200 ml. An internal retained pH gradient was generated and the protein was eluted with 12 column volumes of Polybuffer at 1 ml/min flow rate. FIG. 3 Panel B.

PGK separation achieved by hybrid (external plus retained internal gradient) chromatofocusing on a weak anionic exchanger Mono P HR 5/20 and a simple two component buffer system without using Polybuffers. Linear external elution gradient was generated in 18 column volumes using starting buffer A-5 mM Piperazine, 5 mM TE pH 8.2 and final buffer B-5 mM Piperazine, 5 nM TE pH 5 at 1 ml/min flow rate. It can be seen that the linearity of the effluent pH profile is severely compromised (dotted line). FIG. 3, panel C. PGK separated by external gradient chromatofocusing utilizing the same two component buffer system as in FIG. 3, panel B but on the strong anionic exchanger Mono Q HR 5/5.

The example shows a much better linear effluent pH profile (dotted line) and better separation. Flow rate 1 ml/min, length of the linear external gradient from pH 8.3 to pH 5, 35 column volumes. FIG. 3, panel D. PGK separated by external gradient chromatofocusing employing the four component buffer system of the invention (see Example 2) on Mono Q HR 5/5. Flow rate 1 ml/min, length of elution with external pH gradient 20 column volumes. Note the extremely linear effluent pH profile (dotted line) and the resulting best separation of the protein species.

Example 4

External pH gradient reverse chromatofocusing of a protein mixture on a strong cationic column Mono S HR 5/5 using a broad linear pH gradient from pH 4 to pH 9.5 (FIG. 4B, dotted line) and the invention's four-component buffer system. It is important to note that the STI and β-lactoglobulin are very well separated in this example but difficult to separate on the anionic column over the same pH range using the same buffer system as presented in Example 2. This demonstrates an important reason to have the two capabilities, chromatofocusing and reverse chromatofocusing, available.

Example 5

This example demonstrates a powerful buffering system to be used for separation of charged molecules by external gradient chromatofocusing and reverse chromatofocusing over very wide pH ranges. The external gradient was preprogrammed to maintain a linear pH gradient of 0.10 pH unit per milliliter of eluent (Panel B curves 1, 3). The observed average pH change in both techniques is 0.10 pH unit per milliliter of effluent (panel A curves 1, 3). The external gradient was programmed to form as follows: 1. in chromatofocusing—from 0% B to 90% B in 58 column volumes, from 90 to 100% B in 15 column volumes, followed by 7 column volumes at 100% B (Panel B curve 1); 2. in reverse chromatofocusing—from 100% B to 90% B in 15 column volumes from 90% B to 0% B in 66 column volumes, followed by 7 column volumes at 0% B (Panel B curve 3). The absorbance of the effluent was monitored at 254 nm (Panel A curves 2, 4) to demonstrate the low absorptivity of the buffering species and thus the negligible effect that the buffering system will have on spectroscopic detection of charged molecules upon separation by both techniques. The linear change of the effluent conductivity Panel B curves 2, 4) and linear pH profiles Panel A curves 1,3) both reflect the low interference of Mono Q and Mono S column resins on the shape of the preformed external pH gradients. Flow rate 1 ml/min.

Example 6

Figure 6:
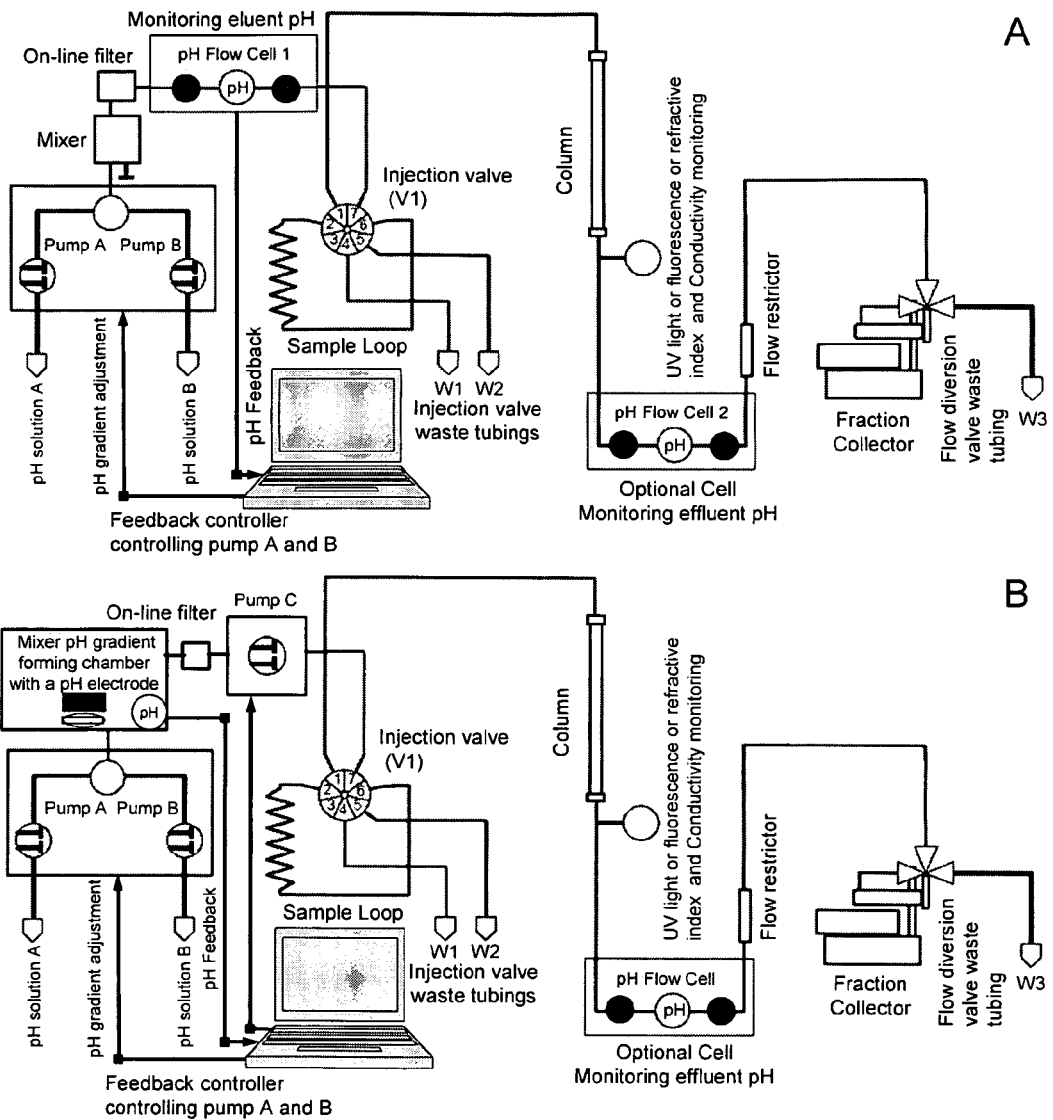
FIG. 6. This figure illustrates a chromatographic system for separation of charged molecules by external pH gradient chromatofocusing and reverse chromatofocusing with an automated feedback system which monitors and adjusts the formation of a pH gradient delivered to an ion exchange column.
Figure 7:
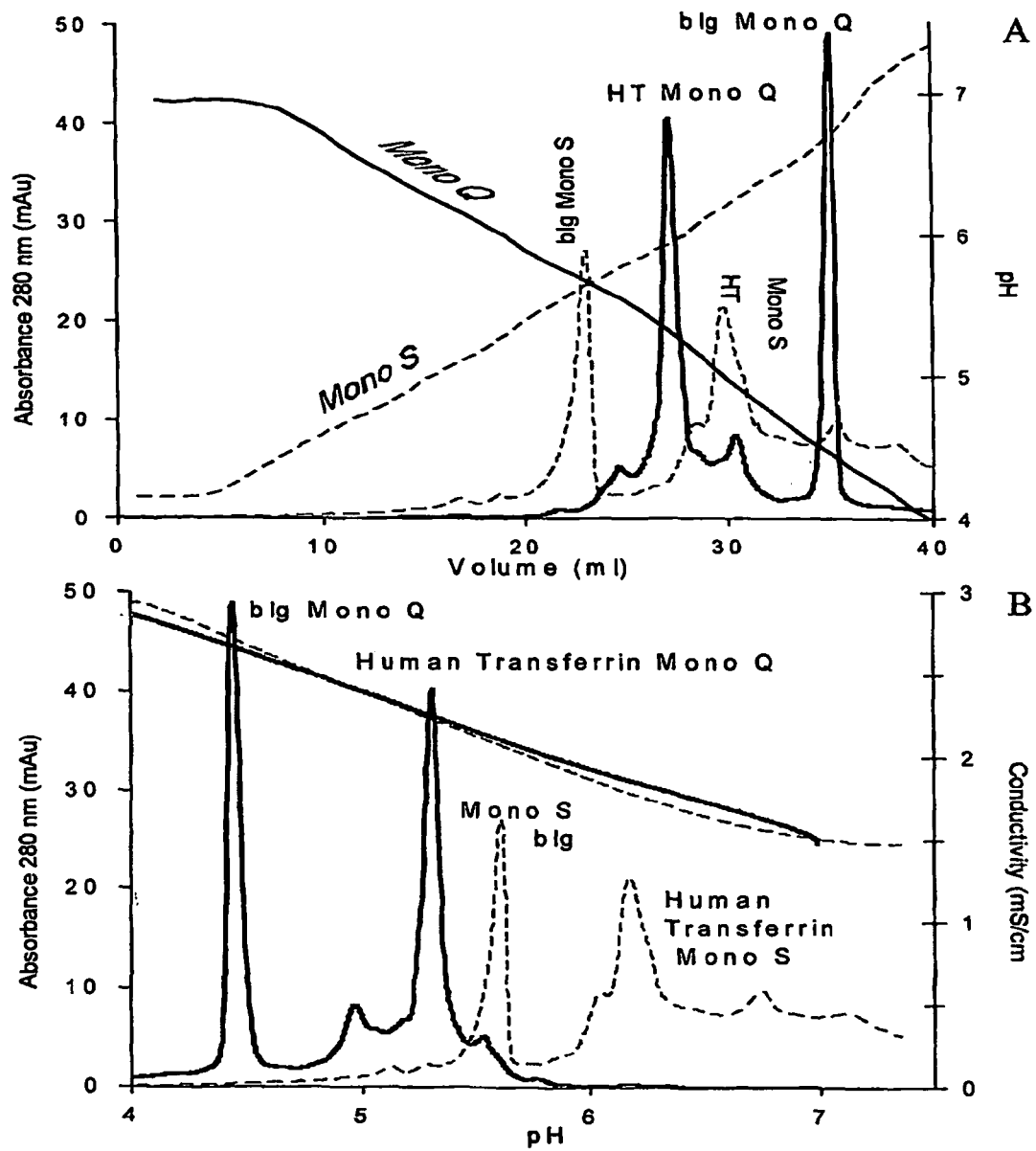
FIG. 7. This figure illustrates an example of combined external gradient chromatofocusing (CEGCF): chromatofocusing followed by reverse chromatofocusing. An anion exchanger column (e.g. Mono Q) and a cation exchanger column (e.g. Mono S) are connected in series. Proteins are initially applied and bound to the anion exchanger at the starting pH. As a pH gradient from pH 7 to pH 4 is developed, the proteins are separated and eluted from the anion exchanger and bound to the cation exchanger. On completion of the chromatofocusing steps, the two columns are disconnected and the proteins are eluted from the cation exchanger by reverse chromatofocusing with a pH gradient from pH 4 to pH 7.5. Panel A illustrates the change of absorbance and pH upon the initial chromatofocusing step (solid lines) followed by the reverse chromatofocusing step (dashed lines). Panel B demonstrates the change of absorbance and conductivity as a function of pH during the first chromatofocusing step (solid lines) followed by the second reverse chromatofocusing step (dashed lines). The CEGCF process can be executed in reverse order starting with EGRCF and finishing with EGCF as well.

This example shows block diagrams of an exemplary chromatographic system for the separation of charged molecules by external pH gradient chromatofocusing and reverse chromatofocusing and includes an automated feedback system which monitors and adjusts the formation of a pH gradient delivered to an ion exchange column (exemplified in FIG. 6). This chromatographic system can utilize either a pH flow cell (FIG. 6, panel A) or a pH electrode integrated in a mixer chamber (FIG. 6, panel B) as a feedback source. In both cases the pH measuring device sends a pH dependent voltage signal to a feedback controller that adjusts the pumping rates of gradient forming solutions in order to correct deviations of the actual pH gradient from a preprogrammed pH gradient. A difference between these systems is that in the mixer chamber system the generated eluent with a time dependent pH is pumped out from the mixer chamber to the ion exchange column by an additional pump. The mixer chamber system can prevent significant pH deviations of the actual pH gradient from the preprogrammed pH gradient because chambers of varying volumes can be used. The larger the volume of the solution that will be titrated in the mixer chamber, the more difficult it is to change the pH. The practical application of this technique allows any pairing of a strong acid solution and a weak base solution or of a strong base solution and a weak acid solution to be used to form the pH gradient.

Example 7

This example illustrates the versatility of the combined external gradient chromatofocusing technique. Tow columns Mono Q a strong anion exchanger column and Mono S a strong cation exchanger column are connected in series and equilibrated at the starting pH 7. In the first step human transferrin and β1g are applied and bound to the anion exchanger. In the second EGCF step a pH gradient from pH 7 to pH 4 is developed, the proteins are separated and eluted from the anion exchanger and immediately bound to the cation exchanger. On completion of the EGCF, the two columns are disconnected from each other and the Mono Q column removed from the flow path. In the final EGRCF step the proteins are eluted from the cation exchanger by a pH gradient developed from pH 4 to pH 7.5. Panel A illustrates the change of absorbance and pH upon the initial EGCF step (solid lines) followed by the EGRCF step (dashed lines). Panel B demonstrates the change of absorbance and conductivity as a function of pH during the first EGCF step (solid lines) followed by the second EGRCF step (dashed lines). The CEGCF process can be executed in reverse order starting with EGRCF and finishing with EGCF as well.

The foregoing detailed description has been given for clearness of understanding only and no unnecessary limitations should be understood therefrom as modifications will be obvious to those skilled in the art.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

What is claimed is:

1. A buffering composition for chromatographically separating charged molecules having different isoelectric points which performs reliably on both strong and weak anionic and cationic columns wherein the at least one buffering component is comprising an aqueous solution of at least three buffering components with or without additional buffering components with widely spaced but overlapping pKas such that when the composition at a predetermined pH is titrated with the composition at a different predetermined pH, the change in the pH of the mixture of the two compositions is proportional to the fraction of the mixture represented by each of the two compositions as characterized by a polynomial derived from titration data; and this polynomial is used to execute a preprogrammed chromatographic method through the software of a liquid chromatography system to either:

supply to an anion exchange adsorbent an eluent formed with a time dependent pH formed from the continuous mixing of a solution at the initial pH containing the at least three buffering components with or without additional buffering components pumped out from a first reservoir with a solution at pH different from the initial pH containing the at least three buffering components pumped out from a second reservoir, wherein the mixing proportions vary to maintain an unretained pH gradient with an externally defined slope; or supply to an anion exchange adsorbent an eluent formed with a time dependent pH formed from the continuous mixing of a solution at the initial pH containing the at least three buffering components with or without additional buffering components pumped out from a first reservoir with a solution at pH different from the initial pH containing the at least three buffering components pumped out from a second reservoir, wherein the mixing proportions vary to maintain an unretained pH gradient with an externally defined slope wherein the at least three buffering components comprise piperazine, 1-methyl piperazine, triethanolamine, bis-tris propane, and formic acid.

2. The composition of claim 1, wherein each of the at least three buffering components contains at least one functionality selected from the group consisting of amino, amido, imino, imido, carboxylic, sulfonic, phosphoric and phosphonic.

3. The composition of claim 1, wherein each of the at least three buffering components is present in a concentration of 0.001 mM to 1,000 mM.

* * * * *

UNITED STATES PATENT AND TRADEMARK OFFICE
CERTIFICATE OF CORRECTION

PATENT NO. : 7,790,025 B2
APPLICATION NO. : 10/556562
DATED : September 7, 2010
INVENTOR(S) : Latchezar I. Tsonev and Allen G. Hirsh It is certified that error appears in the above-identified patent and that said Letters Patent is hereby corrected as shown below:

Column 39, Line 4 "anion" should read --anion or cation--.

Column 39, Line 14 "anion" should read --anion or cation--.

Signed and Sealed this

Twenty-third Day of November, 2010

David J. Kappos
*Director of the United States Patent and Trademark Office*